US009408891B2

(12) United States Patent  
Janmey et al.

(10) Patent No.: US 9,408,891 B2
(45) Date of Patent: Aug. 9, 2016

(54) METHODS OF USING GELSOLIN TO TREAT OR PREVENT BACTERIAL SEPSIS

(75) Inventors: Paul A. Janmey, Media, PA (US); Robert Bucki, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 11/391,540

(22) Filed: Mar. 28, 2006

(65) Prior Publication Data

US 2007/0238668 A1 Oct. 11, 2007

Related U.S. Application Data

(63) Continuation-in-part of application No. 10/574,034, filed as application No. PCT/US2004/037763 on Nov. 12, 2004.

(60) Provisional application No. 60/519,286, filed on Nov. 12, 2003.

(51) Int. Cl.
A61K 38/17 (2006.01)

(52) U.S. Cl.
CPC .................................. A61K 38/1709 (2013.01)

(58) Field of Classification Search
CPC ................................................ A61K 38/1709
USPC ...................................... 435/4; 530/324, 350
See application file for complete search history.

(56) References Cited

U.S. PATENT DOCUMENTS

| | | |
|---|---|---|
| 5,071,773 A | 12/1991 | Evans et al. |
| 5,260,224 A | 11/1993 | Stossel et al. |
| 5,407,821 A | 4/1995 | Breakefield et al. |
| 5,464,817 A | 11/1995 | Stossel et al. |
| 5,508,265 A | 4/1996 | Stossel et al. |
| 5,569,588 A | 10/1996 | Ashby et al. |
| 5,571,511 A | 11/1996 | Fischer |
| 5,580,265 A | 12/1996 | Koblitz et al. |
| 5,593,964 A | 1/1997 | Goldstein et al. |
| 5,656,589 A | 8/1997 | Stossel et al. |
| 5,691,160 A | 11/1997 | Janmey et al. |
| 5,744,303 A | 4/1998 | Iggo et al. |
| 5,750,353 A | 5/1998 | Kopin et al. |
| 5,783,662 A | 7/1998 | Janmey et al. |
| 5,804,427 A | 9/1998 | Davis et al. |
| 5,830,436 A | 11/1998 | Ghio et al. |
| 5,846,743 A | 12/1998 | Janmey et al. |
| 5,925,529 A | 7/1999 | Coughlin et al. |
| 6,040,147 A | 3/2000 | Ridker et al. |
| 6,271,353 B1 | 8/2001 | Nakamura et al. |
| 7,432,308 B2 | 10/2008 | Demeester et al. |
| 7,928,089 B2 | 4/2011 | Morton et al. |
| 8,198,094 B2 | 6/2012 | Stossel et al. |
| 8,440,622 B2 | 5/2013 | Stossel et al. |
| 2002/0103112 A1 | 8/2002 | Ferguson et al. |
| 2003/0083262 A1 | 5/2003 | Hannig et al. |
| 2004/0072261 A1 | 4/2004 | Kostanjevecki et al. |
| 2004/0141961 A1 | 7/2004 | Demeester et al. |
| 2006/0009386 A1 | 1/2006 | Stossel et al. |
| 2007/0087969 A1 | 4/2007 | Ferguson et al. |
| 2007/0238655 A1 | 10/2007 | Bucki et al. |
| 2008/0125370 A1 | 5/2008 | Stossel et al. |
| 2008/0261260 A1 | 10/2008 | Stossel et al. |
| 2009/0258830 A1 | 10/2009 | Thadhani et al. |
| 2010/0021428 A1 | 1/2010 | Stossel et al. |
| 2010/0227807 A1 | 9/2010 | Stossel et al. |
| 2012/0208743 A1 | 8/2012 | Stossel et al. |
| 2013/0230455 A1 | 9/2013 | Stossel et al. |

FOREIGN PATENT DOCUMENTS

| | | |
|---|---|---|
| CA | 2 142 121 A1 | 3/1994 |
| JP | 2004-532386 | 10/2004 |
| WO | WO 91/15770 A1 | 10/1991 |
| WO | WO 91/17170 A1 | 11/1991 |
| WO | WO 94/04704 A1 | 3/1994 |
| WO | WO 94/22465 A1 | 10/1994 |
| WO | WO 95/09645 A1 | 4/1995 |
| WO | WO 00/55350 A1 | 9/2000 |
| WO | WO 02/059604 A2 | 8/2002 |
| WO | WO 03/020213 A2 | 3/2003 |
| WO | WO 03/088811 A2 | 10/2003 |
| WO | WO 2004/023973 A2 | 3/2004 |

(Continued)

OTHER PUBLICATIONS

Angus (Crit. Care. Med. 20(7) S109-S116, 2001).*
Yancey (Obstetrics & Gynecology 87(2), 188-194, 1996).*
Moss Marc [Clinical infectious diseases : an official publication of the Infectious Diseases Society of America,) vol. 41 Suppl 7, pp. S490-S497, 2005].*
Simon Laura J (Contemporary Clinical Trials 28(5), 638-646, 2007).*
Bucki, Robert (Current Protein & Peptide Science, (Dec. 2008) vol. 9, No. 6, pp. 541-551).*
Liao Chia-Jung (Gynecologic Oncology, (Jan. 2011) vol. 120, No. 1, pp. 135-144).*
Osborn, Teresia M (Arthritis Research & Therapy, (2008) vol. 10, No. 5, pp. R117).*
Suhler G (Crit. Care Med. 25, 594-598, 1997).*

(Continued)

*Primary Examiner* — David Lukton
(74) *Attorney, Agent, or Firm* — Wolf, Greenfield & Sacks, P.C.

(57) ABSTRACT

Provided are methods of using gelsolin and active fragments thereof to neutralize, treat or prevent the pathogenic effects of lipoteichoic acid (LTA) toxins released from gram-positive bacteria, including massive activation of inflammatory response in a patient and the resulting lethal septic shock. The provided gelsolin binds to and neutralizes LTA from various bacteria, as well as eukaryotic acidic lysolipids adversely associated with bacterial sepsis and inflammation in the patient, with high affinity, thereby decreasing circulating LTA and the eukaryotic markers, and negating the deleterious biological effects of the gram-positive bacterial infection. Consequently, the provided gelsolin replacement therapy offers a method and compositions for the prevention of bacterial sepsis-induced mortality in the patient.

13 Claims, 9 Drawing Sheets

(56) References Cited

FOREIGN PATENT DOCUMENTS

| | | | |
|---|---|---|---|
| WO | WO 2004/035008 A2 | 4/2004 | |
| WO | WO 2004/082617 A2 | 9/2004 | |
| WO | WO 2005/046454 A3 | 5/2005 | |
| WO | WO 2005/085859 A1 | 9/2005 | |
| WO | WO 2005/112970 A2 | 12/2005 | |
| WO | WO 2007/041245 A2 | 4/2007 | |
| WO | WO 2007/106577 A2 | 9/2007 | |
| WO | WO 2007/109056 A2 | 9/2007 | |
| WO | WO 2009/094194 A2 | 7/2009 | |

OTHER PUBLICATIONS

Extended European Search Report for EP 10185573.2 mailed May 16, 2012.
Extended European Search Report for EP 13186249.2 mailed Feb. 17, 2014.
Office Action mailed Feb. 12, 2014 for U.S. Appl. No. 10/574,034.
Office Action mailed Jul. 9, 2008 for U.S. Appl. No. 11/129,670.
Office Action mailed Mar. 2, 2009 for U.S. Appl. No. 11/129,670.
Office Action mailed Aug. 19, 2009 for U.S. Appl. No. 11/129,670.
Office Action mailed Jul. 16, 2010 for U.S. Appl. No. 11/129,670.
Office Action mailed Aug. 29, 2013 for U.S. Appl. No. 11/129,670.
Office Action mailed May 23, 2014 for U.S. Appl. No. 11/129,670.
Badid et al., Role of myofibroblasts during normal tissue repair and excessive scarring: interest of their assessment in nephropathies. Histol Histopathol. Jan. 2000;15(1):269-80.
Brettschneider et al., Tau protein level in cerebrospinal fluid is increased in patients with early multiple sclerosis. Mult Scler. Jun. 2005;11(3):261-5.
Chavko et al., Lung injury and recovery after exposure to blast overpressure. J Trauma. Oct. 2006;61(4):933-42.
Chebotareva et al., [The role of smooth muscle alpha-actin in development of renal fibrosis in patients with chronic glomerulonephritis]. Ter Arkh. 2006;78(5):17-21.
Chen, Multiple Sclerosis. Chinese Medicine Press. Jun. 30, 2000;67-73.
Dou, Immunocytology and Disease. Chapter 11. Chinese Medical Science and Technology Press. Sep. 30, 2004;404-415.
Grant et al., Reversal of Paralysis and Reduced Inflammation from Peripheral Administration of Amyloid-β in Th1- and Th17-Versions of Experimental Autoimmune Encephalomyelitis. Sci Transl Med. Aug. 1, 2012; 4(145): 145ra105.
Ji et al., Gelsolin levels are increased in the brain as a function of age during normal development in children that are further increased in Down syndrome. Alzheimer Dis Assoc Disord. Oct.-Dec. 2009:23(4):319-22.
KuŁakowska et al., Depletion of plasma gelsolin in patients with tick-borne encephalitis and Lyme neuroborreliosis. Neurodegener Dis. 2011;8(5):375-80.
Maury et al., Homozygosity for the Asn187 gelsolin mutation in Finnish-type familial amyloidosis is associated with severe renal disease. Genomics. Jul. 1992;13(3):902-3.
Pottiez et al., Mass spectrometric characterization of gelsolin isoforms. Rapid Commun Mass Spectrom. Sep. 15, 2010;24(17):2620-4.
Robinson, Amyloid beta reverses MS-like disease in mice. Is it time to reevaluate amyloid elsewhere? Sep. 2012:16-17.
Vasconcellos et al., Coordinated inhibition of actin-induced platelet aggregation by plasma gelsolin and vitamin D-binding protein. Blood. Dec. 15, 1993;82(12):3648-57.
EP 10185573.2, Apr. 1, 2011, Partial European Search.
PCT/US2005/016798, Nov. 18, 2005, Invitation to Pay Additional Fees.
PCT/US2005/016798, Nov. 23, 2006, International Preliminary Report on Patentability.
EP 07753226.5, Feb. 17, 2009, Extend European Search Report.
PCT/US2007/006581, Aug. 11, 2008, International Search Report and Written Opinion.
PCT/US2007/006581, Sep. 25, 2008, International Preliminary Report on Patentability.
EP 07753102.8, Jun. 10, 2009, Extended European Search Report.
PCT/US2007/006451, Sep. 25, 2007, International Search Report and Written Opinion.
PCT/US2007/006451, Sep. 25, 2008, International Preliminary Report on Patentability.
EP 04810817.9, Jun. 10, 2010, Supplemental European Search Report.
PCT/US2004/037763, May 5, 2005, Invitation to Pay Additional Fees.
PCT/US2004/037763, Aug. 31, 2005, International Search Report and Written Opinion.
PCT/US2004/037763, May 26, 2006, International Preliminary Report on Patentability.
EP 09703176.9, Jan. 17, 2011, Extended European Search Report.
PCT/US2009/000452, Mar. 16, 2009, Invitation to Pay Additional Fees.
PCT/US2009/000452, May 18, 2009, International Search Report and Written Opinion.
PCT/US2009/000452, Aug. 5, 2010, International Preliminary Report on Patentability.
Office Communication mailed Jul. 23, 2010 for U.S. Appl. No. 10/574,034.
Office Communication mailed Apr. 7, 2011 for U.S. Appl. No. 10/574,034.
Partial European Search Report for EP 10185573.2 mailed Apr. 1, 2011.
Invitation to Pay Additional Fees for PCT/US2005/016798 mailed Nov. 18, 2005.
International Preliminary Report on Patentability for PCT/US2005/016798 mailed Nov. 23, 2006.
Extended European Search Report for EP 07753226.5 mailed Feb. 17, 2009.
International Search Report and Written Opinion for PCT/US2007/006581 mailed Aug. 11, 2008.
International Preliminary Report on Patentability for PCT/US2007/006581 mailed Sep. 25, 2008.
Extended European Search Report for EP 07753102.8 mailed Jun. 10, 2009.
International Search Report and Written Opinion for PCT/US2007/006451 mailed Sep. 25, 2007.
International Preliminary Report on Patentability for PCT/US2007/006451 mailed Sep. 25, 2008.
Supplemental European Search Report for EP 04810817.9 mailed Jun. 10, 2010.
Invitation to Pay Additional Fees for PCT/US2004/037763 mailed May 5, 2005.
International Search Report and Written Opinion for PCT/US2004/037763 mailed Aug. 31, 2005.
International Preliminary Report on Patentability for PCT/US2004/037763 mailed May 26, 2006.
Extended European Search Report for EP 09703176.9 mailed Jan. 17, 2011.
Invitation to Pay Additional Fees for PCT/US2009/000452 mailed Mar. 16, 2009.
International Search Report and Written Opinion for PCT/US2009/000452 mailed May 18, 2009.
International Preliminary Report on Patentability for PCT/US2009/000452 mailed Aug. 5, 2010.
GenBank Submission; NIH/NCBI, Accession No. 1211330A; Kwiatkowski et al.; Oct. 1, 1996. Last accessed Feb. 3, 2005 at http:ncbi.nlm.nih.gov/entrez/viewer.fcgi?db=protein&val=225304. 2 pages.
GenBank Submission; NIH/NCBI, Accession No. CAA28000; Kwiatkowski et al.; Mar. 21, 1995. Last accessed Feb. 3, 2005 at http:ncbi.nlm.nih.gov/entrez/viewer.fcgi?db=protein&val=736249. 2 pages.
GenBank Submission; NIH/NCBI, Accession No. X04412.1; Kwiatkowski et al.; Oct. 7, 2008.

(56) References Cited

OTHER PUBLICATIONS

[No Author Listed] "Risk". Dorlands Medical Dictionary. Merck Source. Last accessed on Jun. 29, 2009 available at www.mercksource.com/pp/us/cns/snc_hl_dorlands_split.jsp?pg=/ppdocs/us/common/dorlands/dorland/seven/000093452.html, 2009. 2 pages.
[No Author Listed] "Risk". Medical Dictionary. Last accessed on Jun. 29, 2009 available at www.medicaldictionaryweb.com/Rish-definition/2009. 1 page.
[No Author Listed] "Risk". Rogets II The New Thesaurus NY, Expanded Edition. Houghton Mifflin Company. New York 1988:843.
Adams et al., Fibrin mechanisms and functions in nervous system pathology. Mol Interv. Jun. 2004;4(3):163-76.
Aidinis et al., Cytoskeletal rearrangements in synovial fibroblasts as a novel pathophysiological determinant of modeled rheumatoid arthritis. PLoS Genet. Oct. 2005;1(4):e48. Epub Oct. 28, 2005. 12 pages.
Barnard et al., Targeted deletion of gelsolin potentiates endotoxin-induced murine lung vascular leak. FASEB. 2004;18(4-5):A352. Abstract 233.8.
Beddhu et al., Inflammation and inverse associations of body mass index and serum creatinine with mortality in hemodialysis patients. J Ren Nutr. Nov. 2007;17(6):372-80.
Bochicchio et al., Reclassification of urinary tract infections in critically ill trauma patients: a time-dependent analysis. Surg Infect (Larchmt). 2003 Winter;4(4):379-85. Abstract only.
Bucki et al., Antibacterial activities of rhodamine B-conjugated gelsolin-derived peptides compared to those of the antimicrobial peptides cathelicidin LL37, magainin II, and melittin. Antimicrob Agents Chemother. May 2004;48(5):1526-33.
Bucki et al., Bacterial endotoxin as inhibitor of the enzymatic activity of human thrombin. Eur J Haematol. Jun. 2006;76(6):510-5. Epub Mar. 9, 2006.
Bucki et al., Extracellular gelsolin binds lipoteichoic acid and modulates cellular response to proinflammatory bacterial wall components. J Immunol. Oct. 1, 2008;181(7):4936-44.
Bucki et al., Inactivation of endotoxin by human plasma gelsolin. Biochemistry. Jun. 19, 2005;44(28):9590-7.
Candiano et al., Gelsolin secretion in interleukin-4-treated bronchial epithelia and in asthmatic airways. Am J Respir Crit Care Med. Nov. 1, 2005;172(9):1090-6. Epub Aug. 11, 2005.
Chauhan et al., Binding of gelsolin, a secretory protein, to amyloid beta-protein. Biochem Biophys Res Commun. May 10, 1999;258(2):241-6.
Cirioni et al., Potential therapeutic role of histatin derivative P-113d in experimental rat models of Pseudomonas aeruginosa sepsis. J Infect Dis. Jul. 15, 2004;190(2):356-64. Epub Jun. 21, 2004.
Cohen et al., Therapeutic potential of plasma gelsolin administration in a rat model of sepsis. Cytokine. Jun. 2011;54(3):235-8. Epub Mar. 21, 2011.
Dinubile et al., Decreased gelsolin levels are associated with interstitial pneumonia after allogenic BMT. Blood. 1998;92(Suppl):683a. Abstract 2814.
Erukhimov et al., Actin-containing sera from patients with adult respiratory distress syndrome are toxic to sheep pulmonary endothelial cells. Am J Respir Crit Care Med. Jul. 2000;162(1):288-94.
Fouque et al., A proposed nomenclature and diagnostic criteria for protein-energy wasting in acute and chronic kidney disease. Kidney Int. Feb. 2008;73(4):391-8. Epub Dec. 9, 2007.
Goetzl, Pleiotypic mechanisms of cellular responses to biologically active lysophospholipids. Prostaglandins. Apr. 2001;64(1-4):11-20.
Güntert et al., Plasma gelsolin is decreased and correlates with rate of decline in Alzheimer's disease. J Alzheimers Dis. 2010;21(2):585-96. Abstract only.
Haddad et al., Angiopathic consequences of saturating the plasma scavenger system for actin. Proc Natl Acad Sci U S A. Feb. 1990;87(4):1381-5.
Hartung et al., Inflammatory mediators in demyelinating disorders of the CNS and PNS. J Neuroimmunol. Oct. 1992;40(2-3):197-210.
Himmelfarb et al., The elephant in uremia: oxidant stress as a unifying concept of cardiovascular disease in uremia. Kidney Int. Nov. 2002;62(5):1524-38.
Hsueh et al., Hypertension, the endothelial cell, and the vascular complications of diabetes mellitus. Hypertension. Aug. 1992;20(2):253-63.
Hyde et al., Mortality and bacteriology of sepsis following cecal ligation and puncture in aged mice. Infect Immun. Mar. 1990;58(3):619-24.
Ito et al., Depression of plasma gelsolin level during acute liver injury. Gastroenterology. May 1992;102(5):1686-92.
Janmey et al., Functional comparison of villin and gelsolin. Effects of Ca2+, KCl, and polyphosphoinositides. J Biol Chem. Nov. 15, 1988;263(32):16738-43.
Jensen et al., Features of endothelial dysfunction in early diabetic nephropathy. Lancet. Mar. 4, 1989;1(8636):461-3.
Jordan et al., Gelsolin is depleted in post-shock mesenteric lymph. J Surg Res. Nov. 2007;143(1):130-5. doi: 10.1016/j.jss.2007.04.017.
Kalantar-Zadeh et al., A malnutrition-inflammation score is correlated with morbidity and mortality in maintenance hemodialysis patients. Am J Kidney Dis. Dec. 2001;38(6):1251-63.
Kalantar-Zadeh et al., Effect of malnutrition-inflammation complex syndrome on EPO hyporesponsiveness in maintenance hemodialysis patients. Am J Kidney Dis. Oct. 2003;42(4):761-73.
Kaysen et al., Longitudinal and cross-sectional effects of C-reactive protein, equilibrated normalized protein catabolic rate, and serum bicarbonate on creatinine and albumin levels in dialysis patients. Am J Kidney Dis. Dec. 2003;42(6):1200-11.
Kent et al., A monoclonal antibody to alpha 4 integrin suppresses and reverses active experimental allergic encephalomyelitis. J Neuroimmunol. Apr. 1995;58(1):1-10.
Kulakowska et al., Gelsolin concentration in cerebrospinal fluid from patients with multiple sclerosis and other neurological disorders. Eur J Neurol. Jun. 2008;15(6):584-8.
KuŁakowska et al., Hypogelsolinemia, a disorder of the extracellular actin scavenger system, in patients with multiple sclerosis. BMC Neurol. Nov. 1, 2010;10:107. 8 pages.
Kwiatkowski et al., Identification of critical functional and regulatory domains in gelsolin. J Cell Biol. May 1989;108(5):1717-26.
Kwiatkowski et al., Isolation and properties of two actin-binding domains in gelsolin. J Biol Chem. Dec. 5, 1985;260(28):15232-8.
Lazarus et al., Role of bioincompatibility in dialysis morbidity and mortality. Am J Kidney Dis. Dec. 1994;24(6):1019-32.
Lee et al., Plasma gelsolin and circulating actin correlate with hemodialysis mortality. J Am Soc Nephrol. May 2009;20(5):1140-8. Epub Apr. 23, 2009.
Lee et al., Plasma Gelsolin Depletion and Circulating Actin in Sepsis: A Pilot Study. PLoS One. 2008;3(11):e3712. doi:10.1371/journal.pone.0003712. 5 pages.
Lee et al., Plasma Gelsolin is a Critical Pro-Survival Factor in Sepsis. American Thoracic Society. 2005. Last accessed Feb. 15, 2012 at http://www.mindcull.com/data/american-thoracic-society/ats-2005-american-thoracic-soci . . . Abstract only. 1 page.
Lee et al., Plasma gelsolin is a marker and therapeutic agent in animal sepsis. Crit Care Med. Mar. 2007;35(3):849-55.
Lee et al., The potential role of plasma gelsolin in dialysis-related protein-energy wasting. Blood Purif. 2010;29(2):99-101. Epub Jan. 8, 2010.
Lind et al., Depression of gelsolin levels and detection of gelsolin-actin complexes in plasma of patients with acute lung injury. Am Rev Respir Dis. Aug. 1988;138(2):429-34.
Lind et al., Human plasma gelsolin binds to fibronectin. J Biol Chem. Nov. 10, 1984;259(21):13262-6.
Löfberg et al., Serum gelsolin and rhabdomyolysis. J Neurol Sci. May 7, 1998;157(2):187-90.
Matsumoto et al., Diagnosis of sepsis based on the host response. The Official Journal of Japanese Society of Laboratory Medicine. 1999;47(6):494-500. Japanese language reference.
Matsuoka et al., Novel therapeutic approach for the treatment of Alzheimer's disease by peripheral administration of agents with an affinity to beta-amyloid. J Neurosci. Jan. 1, 2003;23(1):29-33.

(56) References Cited

OTHER PUBLICATIONS

McIntyre et al., Patients receiving maintenance dialysis have more severe functionally significant skeletal muscle wasting than patients with dialysis-independent chronic kidney disease. Nephrol Dial Transplant. Aug. 2006;21(8):2210-6. Epub Feb. 27, 2006.
Mezzano et al., Endothelial cell markers in chronic uremia: relationship with hemostatic defects and severity of renal failure. Thromb Res. Dec. 15, 1997;88(6):465-72.
Mezzano et al., Inflammation, not hyperhomocysteinemia, is related to oxidative stress and hemostatic and endothelial dysfunction in uremia. Kidney Int. Nov. 2001;60(5):1844-50.
Mitch et al., Mechanisms of muscle wasting. The role of the ubiquitin-proteasome pathway. N Engl J Med. Dec. 19, 1996;335(25):1897-905.
Morgan, Risk factors for infection in the trauma patient. J Natl Med Assoc. Dec. 1992;84(12):1019-23.
Myers et al., Collagen-induced arthritis, an animal model of autoimmunity. Life Sci. 1997;61(19):1861-78.
Nandakumar et al., Efficient promotion of collagen antibody induced arthritis (CAIA) using four monoclonal antibodies specific for the major epitopes recognized in both collagen induced arthritis and rheumatoid arthritis. J Immunol Methods. Sep. 2005;304(1-2):126-36.
Ni et al., The ubiquitin-proteasome pathway mediates gelsolin protein downregulation in pancreatic cancer. Mol Med. Sep.-Oct. 2008;14(9-10):582-9.
Nollet et al., Protection of just weaned pigs against infection with F18+ *Escherichia coli* by nonimmune plasma powder. Vet Microbiol. Feb. 23, 1999;65(1):37-45.
Osborn et al., Decreased levels of the gelsolin plasma isoform in patients with rheumatoid arthritis. Arthritis Res Ther. 2008;10(5):R117. Epub Sep. 27, 2008. 9 pages.
Osborn et al., Modifications of cellular responses to lysophosphatidic acid and platelet-activating factor by plasma gelsolin. Am J Physiol Cell Physiol. Apr. 2007;292(4):C1323-30. Epub Nov. 29, 2006.
Otero-Antón et al. Cecal ligation and puncture as a model of sepsis in the rat: influence of the puncture size on mortality, bacteremia, endotoxemia and tumor necrosis factor alpha levels. Eur Surg Res. 2001;33(2):77-9.
Overhaus et al., Mechanisms of polymicrobial sepsis-induced ileus. Am J Physiol Gastrointest Liver Physiol. Sep. 2004;287(3):G685-94.
Owen et al., The urea reduction ratio and serum albumin concentration as predictors of mortality in patients undergoing hemodialysis. N Engl J Med. Sep. 30, 1993;329(14):1001-6.
Semba et al., Low serum selenium is associated with anemia among older adults in the United States. Eur J Clin Nutr. Jan. 2009;63(1):93-9. Published online Sep. 5, 2007. doi: 10.1038/sj.ejcn.1602889.
Smith et al., Evidence for two pathways of protein kinase C induction of 2ar expression: correlation with mitogenesis. J Cell Physiol. Apr. 1989;139(1):189-95.
Smith et al., Quantitative measurement of plasma gelsolin and its incorporation into fibrin clots. J Lab Clin Med. Aug. 1987;110(2):189-95.
Trautner et al., Role of biofilm in catheter-associated urinary tract infection. Am J Infect Control. May 2004;32(3):177-83. doi: 10.1016/j.ajic.2003.08.005.
Walker et al., Enhanced Pseudomonas aeruginosa biofilm development mediated by human neutrophils. Infect Immun. Jun. 2005;73(6):3693-701.
Wanner et al., Atorvastatin in patients with type 2 diabetes mellitus undergoing hemodialysis. N Engl J Med. Jul. 21, 2005;353(3):238-48.
Witke et al., Hemostatic, inflammatory, and fibroblast responses are blunted in mice lacking gelsolin. Cell. Apr. 7, 1995;81(1):41-51.
Workeneh et al., Review of muscle wasting associated with chronic kidney disease. Am J Clin Nutr. Apr. 2010;91(4):1128S-1132S. Epub Feb. 24, 2010.
Yamamoto et al., Human plasma gelsolin binds adenosine triphosphate. J Biochem. Oct. 1990;108(4):505-6.

Yin et al., Structure and biosynthesis of cytoplasmic and secreted variants of gelsolin. J Biol Chem. Apr. 25, 1984;259(8):5271-6.
Zuo et al., [Bacteriological study of chronic sinusitis]. Zhonghua Er Bi Yan Hou Tou Jing Wai Ke Za Zhi. Jul. 2005;40(7):524-7. English Abstract.
Bannerman et al., "Increased Levels of LPS-Binding Protein in Bovine Blood and Milk Following Bacterial Lipopolysaccharide Challenge," *J. Dairy Sci.*, vol. 86, pp. 3128-3137 (2003).
Becker et al., "The antimicrobial activity of the cathelicidin LL37 is inhibited by F-actin bundles and restored by gelsolin," *Amer. Journal of Respiratory Cell and Molecular Biology*, vol. 28, No. 4, (2003), pp. 478-484.
Berer et al., "Are the serum levels of endotoxin-binding proteins reliable predictors of complications in the course of peritonitis?," *European Journal of Clinical Investigation*, vol. 20, pp. 66-71 (1990).
Berger et al, "Evidence for endotoxin binding capacity of human Gc-globulin and transferrin," *Clinica Chimica Acta*, vol. 163, pp. 289-299 (1987).
Beutler et al, "Sepsis and evolution of the innate immune response," *Crit Care Med*, vol. 29, No. 7, pp. S2-S7 (2001).
Bowman et al., "Cultured Astrocytes Express Toll-Like Receptors for Bacterial Products," *Glia*, vol. 43, pp. 281-291 (2003).
Bsibsi et al., "Broad Expression of Toll-Like Receptors in the Human Central Nervous System," *J Neuropathology Exp. Neurol.*, vol. 61, No. 11, pp. 1013-1021 (2002).
Bosshart et al., Endotoxin-neutralizing effects of histidine-rich peptides, *FEBS Letters*, vol. 553, pp. 135-140 (2003).
Brandenburg et al., "Physicochemical properties of bacterial glycopolymers in relation to bioactivity," *Carbohydrate Research*, vol. 338, pp. 2477-2489 (2003).
Casas et al., "Reconstituted High-Density Lipoprotein Reduces LPS-Stimulated TNF," *J. Sur. Res.*, vol. 59, pp. 544-552 (1995).
Christofidou-Solomidou et al., "Changes in plasma gelsolin concentration during acute oxidant lung injury in mice," *Lung*, vol. 180, No. 2, (2002) pp. 91-104.
Christofidou-Solomidou et al., "Recombinant Plasma Gelsolin Diminishes the Acute Inflammatory Response to Hyperoxia in Mice," *J. Invest. Med.*, vol. 50, No. 1, pp. 54-60 (2002).
Cunningham et al, "Cell Permeant Polyphosphoinostide-binding Peptides that Block Cell Motility and Actin Assembly," *J. Biol. Chem.*, vol. 276, pp. 43390-43399 (2001).
Dahl et al., "Plasma concentration of Gc-globulin is associated with organ dysfunction and sepsis after injury," *Crit. Care Med*, vol. 31, No. 1, pp. 152-156 (2003).
Dahl et al, "Plasma Gelsolin is Reduced in Trauma Patients," *Shock*, vol. 12, pp. 102-104 (1999).
Dahl et al., "Serum Gc-globulin in the early course of multiple trauma," *Crit. Care Med.*, vol. 26, No. 2, pp. 285-289 (1998).
DiNubile et al, "Prognostic implications of declining plasma gelsolin levels after allogeneic stem cell transplantation," *Blood*, vol. 100, No. 13, pp. 4367-4371 (2002).
Erridge et al., "Structure and function of lipopolysaccharides," *Microbes Infect.*, vol. 4, No. 8, pp. 837-851 (2002).
Faure et al., "Bacterial Lipopolysaccharide Activates NF-kB through Toll-like Receptor 4 (TLR-4) in Cultured Human Derman Endothelial Cells," *J. Biol. Chem.*, vol. 275, No. 15, pp. 11058-11063 (2000).
Flanagan et al., "The S tructure of Divalent Cation-Induced Aggregates of $PIP_2$ and their Alteration of Gelsolin and Tau," *Biophysical Journal*, vol. 73, pp. 1440-1447 (1997).
Ginsburg, "Role of lipoteichoic acid in infection and inflammation," *Lancet Infect. Diseases*, vol. 2, pp. 171-179 (2002).
Goetzl et al., "Gelsolin Binding and Cellular Presentation of Lysophosphatidic Acid," *J. Biol. Chem.*, vol. 275, No. 19, pp. 14573-14578 (2000).
Goldschmidt-Clermont et al., "Role of Group-specific Component (Vitamin D Binding Protein) in Clearance of Actin from the Circulation in the Rabbit," *J. Clin. Invest.*, vol. 81, pp. 1519-1527 (1988).
Gutsmann et al., "Dual Role of Lipopolysacharide (LPS)-Binding Protein in Neutralization of LS and Enhancement of LPS-Induced Activation of Mononuclear Cells," *Infect. and Immun.*, vol. 69, No. 11, pp. 6942-6950 (2001).

(56) References Cited

OTHER PUBLICATIONS

Harris et al., "Lipoprotein-bound LPS induces cytokine tolerance in hepatocytes," *J. of Endotoxin Res.*, vol. 9, pp. 45-50 (2003).
Hattar et al., "Lipoteichoic acid (LTA) from *Staphylococcus aureus* stimulates human neutrophil cytokine release by a CD14-dependent, Toll-like-receptor-independent mechanism: Autocrine role of tumor necrosis factor-a in mediating LTA-induced interleukin-8 generation," *Crit. Care Med.*, vol. 34, pp. 835-841 (2006).
Hayter et al., "Neutron Scattering Analysis of Bacterial Lipopolysaccharide Phase Structure," *J. Biol. Chem.*, vol. 262, pp. 5100-5105 (1987).
Huang, "Temporal Association Between Serum Gelsolin Levels and Clinical Events in a Patient With Severe Falciaparum Malaria," *Clinical Infectious Diseases*, vol. 24, pp. 951-954 (1997).
Hummell et al., "Bacterial Lipoteichoic Acid Sensitizes Host Cells for Destruction by Autologous Complement," *J. Clin. Invest.*, vol. 77, No. 5, pp. 1533-1538 (1986).
Igarashi et al., "Sphingosine-Phosphate Content in the Plasma of Platelet Concentrates Correlates with Poor Platelet Increments after Transfusion and with occurrences of Transfusion Reactions in Patients," *Am. J. Hematol.*, vol. 57, pp. 261-262 (1998).
Jammey et al., Modulation of gelsolin function by phosphatidylinositol 4,5-bisphosphate, *Nature*, vol. 325, pp. 362-364 (1987).
Jammey et al., "Interactions of Gelsolin and Gelsolin-Actin Complexes with Actin. Effects of Calcium on Actin Nucleation, Filament Severing, and End Blocking," *Biochemistry*, vol. 24, pp. 3714-3723 (1985).
Jammey et al., "Polyphosphoinositide Micelles and Polyphosphoinositide-containing Vesicles Dissociate Endogenous Gelsolin-Actin Complexes and Promote Actin Assembly from the Fast-growing End of Actin Filaments Blocked by Gelsolin," *J. Biol. Chem.*, vol. 262, pp. 12228-12236 (1987).
Jammey et al., "Phosphoinositide-binding Peptides Derived from the Sequences of Gelsolin and Villin," *J. Biol. Chem.*, vol. 267, pp. 11818-11823 (1992).
Jammey et al., "Capacity of Human Serum to Depolymerize Actin Filaments," *Blood*, vol. 70, pp. 524-530 (1987).
Jammey et al., "Deconstructing gelsolin: identifying sites that mimic or alter binding to actin and phosphoinositides," Chem. Biol., vol. 5, pp. R81-R85 (1998).
Jorgensen et al., "Peptidoglycan and Lipoteichoic Acid Modify Monocyte Phenotype in Human Whole Blood," *Clin. Diagn. Lab. Immunol.*, vol. 8, pp. 515-521 (2001).
Kawamura et al., "Lipoteichoic Acid-Induced Neutrophil Adhesion via E-Selectin to Human Umbilical Vein Endothelial Cells (HUVECs)," *Biochem. Biophys. Res. Commun.*, vol. 217, pp. 1208-1215 (1995).
Kouyama et al., "Fluorimetry Study of N-(1-Pyrenyl)iodoacetamide-Labelled F-Actin," *Eur. J. Biochem.*, vol. 114, pp. 33-38 (1981).
Kwiatkowski et al., "Plasma and cytoplasmic gelsolins are encoded by a single gene and contain a duplicated actin-binding domain," *Nature*, vol. 323, pp. 455-458 (1986).
Kwiatkowski et al., "Functions of gelsolin: motility, signaling, apoptosis, cancer," *Curr. Opin. Cell Biol.*, vol. 11, pp. 103-108 (1999).
Kwiatkowski et al., "Muscle is the Major Source of Plasma Gelsolin," *J. Biol. Chem.*, vol. 263, pp. 8239-8243 (1988).
Lee et al., "The Extracellular Actin-Scavenger System and Actin Toxicity," *N. Engl. J. Med.*, vol. 326, pp. 1335-1341 (1992).
Lee et al., "Relationship of Plasma Gelsolin Levels to Outcomes in Critically Ill Surgical Patients," *Annals of Surgery*, vol. 243, No. 3, pp. 399-403 (2006).
Lee et al., "Plasma Gelsolin Levels Predict the Outcomes of Critically Ill Patients in Surgical Intensive Care Unit", American Thoracic Society International Conference, A627, vol. 169, No. 7, Apr. 2004 (ATS 2004—Orlando)—Abstract.
Li et al., "The critical micelle concentrations of Lysophosphatidic acid and sphirigosylphosphorylcholine," *Chem. Phys. Lipids*, vol. 130, pp. 197-201 (2004).
Liepina et al., "Molecular Dynamics Study of a Gelsolin-Derived Peptide Binding to a Lipid Bilayer Containing Phosphatidylinositol 4,5-Bisphosphate," *Biopolymers*, vol. 71, pp. 49-70 (2003).
Lind et al., "Role of Plasma Gelsolin and the Vitamin D-binding Protein in Clearing Actin from the Circulation," *J. Clin. Invest.*, vol. 78, pp. 736-742 (1986).
Masover et al., "The effect of growth and urea concentration on ammonia production by a urea-hydrolysing mycoplasma (Ureaplasma urealyticum," J. Gen. Microbiol., vol. 98 (1977).
Mathison et al., "Plasma Lipopolysaccharide (LPS)-Binding Protein, A Key Component in Macrophage Recognition of Gram-Negative LPS," *J. Immun.*, vol. 149, pp. 200-206 (1992).
Meerschaert et al., "Gelsolin and functionally similar actin-binding proteins are regulated by lysophosphatidic acid," *EMBO Journal*, vol. 17, pp. 5923-5932 (1998).
Mertsola et al., "Release of endotoxin after antibiotic treatment of Gram-negative bacterial meningitis," *Ped. Inf. Dis. J.*, vol. 8, pp. 904-906 (1989).
Mintzer et al., "Lysophosphatidic acid and lipopolysaccharide bind to the $PIP_2$-binding domain of gelsolin," *Biochem. Biophysic. Acta*, vol. 1758, pp. 85-98 (2006).
Mounzer et al., "Relationship of Admission Plasma Gelsolin Levels to Clinical Outcomes in Patients after Major Trauma," *Am. J Respir. Crit. Care Med.*, vol. 160, pp. 1673-1681 (1999).
Nugent et al., "Sphingosine-1-phosphate: characterization of its inhibition of platelet aggregation," *Platelets*, vol. 11, pp. 226-232 (2000).
Overland et al., "Lipoteichoic Acid is a Potent Inducer of Cytokine Production in Rat and Human Kupffer Cells In Vitro," *Sur. Infect.*, vol. 4, No. 2, pp. 181-189 (2003).
Riedemann et al., "The enigma of sepsis," *J Clin. Invest.*, vol. 112, pp. 460-467 (2003).
Rogers et al., "Relationship of Gelsolin Levels to Outcomes in Critically Ill Patients", Journal of Surgical Research, vol. 107, No. 2, (Oct. 2002), (ISSN 0022-4804)—Abstract.
Rothenbach et al., "Recombinant plasma gelsolin infusion attenuates burn-induced pulmonary microvascular dysfunction," *J. Appl. Physiol.*, vol. 96, pp. 25-31 (2004).
Rustici et al., "Molecular Mapping and Detoxification of the Lipid A Binding Site by Synthetic Peptides," Science, vol. 259, pp. 361-365 (1993).
Salat et al., "The Relevance of Plasminogen Activator Inhibitor 1 (PAI-1) as a Marker for the Diagnosis of Hepatic Veno-Occlusive Disease in Patients after Bone Marrow Transplantation," *Leukemia and Lymphoma*, vol. 33, pp. 25-32 (1999).
Saura et al., "Microglial apolipoprotein E and astroglial apolipoprotein J expression in vitro: opposite effects of lipopolysaccharide," *J. Neurochem.* vol. 85, pp. 1455-1467 (2003).
Scarborough et al., "Aggregation of Platelets by Muscle Actin. A Multivalent Interaction Model of Platelet Aggregation by ADP," *Biochem. Biophys. Res. Comm.*, vol. 100, pp. 1314-1319 (1981).
Schroder et al., "Lipoteichoic Acid (LTA) of *Streptococcus pneumoniae* and *Staphylococcus aureus* Activates Immune Cells via Toll-like Receptor (TLR)-2, Lipopolysaccharide-binding Protein (LBP), and CD14, whereas TLR-4 and MD-2 are Not Involved," *J. Biol. Chem*. vol. 278, pp. 15587-15594 (2003).
Schultz et al., "Animal and human models for sepsis," *Ann. Med.*, vol. 34, pp. 573-581 (2002).
Sheu et al., "Mechanisms involved in the antiplatelet activity of *Escherichia coli* lipopolysaccharide in human platelets," *Br. J. Haemat.*, vol. 103, pp. 29-38 (1998).
Shimazu et al., "MD-2, a Molecule that Confers Lipopolysaccharide Responsiveness on Toll-like Receptor 4," *J. Exp. Med.*, vol. 189, pp. 1777-1782 (1999).
Smith et al., "Decreased Plasma Gelsolin Levels in Patients with Plasmodium falciparum Malaria: A Consequence of Hemolysis?" *Blood*, vol. 72, pp. 214-218 (1988).
Spudich et al., "The Regulation of Rabbit Skeletal Muscle Contraction, I. Biochemical studies of the interaction of the tropomyosin-troponin complex with actin and the proteolytic fragments of myosin," *J. Biol. Chem.*, vol. 246, pp. 4866-4871 (1971).

(56) References Cited

OTHER PUBLICATIONS

Stossel, Thomas P., "From Signal to Pseudopod, How Cells Control Cytoplasmic Actin Assembly," *J. Biol. Chem.*, vol. 264, pp. 18261-18264 (1989).
Suhler et al., "Decreased plasma gelsolin concentrations in acute liver failure, myocardial infarction, septic shock, and myonecrosis," *Crit. Care Med.*, vol. 25, pp. 594-598 (1997).
Sun et al., "Gelsolin, a Multifunctional Actin Regulatory Protein," *J. Biol. Chem.*, vol. 274, pp. 33179-33182 (1999).
Tauber et al., "Antibiotic therapy, Endotoxin Concentration in Cerebrospinal Fluid, and Brain Edema in Experimental *Escherichia coli* Meningitis in Rabbits," *J. Infect. Diseases*, vol. 156, pp. 456-462 (1987).
Thomas et al., "Biopanning of endotoxin-specific phage displayed peptides," *Biochem. and Biophys. Res. Comm.*, vol. 307, pp. 133-138 (2003).
Tobias et al., "Control of Lipopolysaccharide-High-Density Lipoprotein Interactions by an Acute-Phase Reactant in Human Serum," *Infection and Immun.*, vol. 50, pp. 73-76 (1985).
Tobias et al., "Isolation of a lipopolysaccharide-binding acute phase reactant from rabbit serum," *J. Exp. Med.*, vol. 164, pp. 777-793 (1986).
Tuominen et al., "Fluorescent phosphoinositide derivatives reveal specific binding of gelsolin and other actin regulatory proteins to mixed lipid bilayers," *Eur. J. Biochem.*, vol. 263, pp. 85-92 (1999).
Van Oosten et al., "Scavenger receptor-like receptors for the binding of lipopolysaccharide and lipoteichoic acid to liver endothelial and Kupffer cells," *J. Endotoxin Res.*, vol. 7, pp. 381-384 (2001).
Villa et al., "Pattern of Cytokines and Pharmacomodulation in Sepsis Induced by Cecal Ligation and Puncture Compared with that Induced by Endotoxin," *Clin. Diag. Lab. Immun.*, vol. 2, pp. 549-553 (1995).
Vreugdenhil et al., "Lipopolysaccharide (LPS)-Binding Protein Mediates LPS Detoxification by Chylomicrons," *J. Immun.*, vol. 170, pp. 1399-1405 (2003).
Wang et al., "HMG-1 as a Late Mediator of Endotoxin Lethality in Mice," *Science*, vol. 285, pp. 157-288 (1999).
Ware et al., "The Acute Respiratory Distress Syndrome," *N. Engl. J. Med.*, vol. 342, pp. 1334-1349 (2000).
Watson et al., "Genetic Control of Responses to Bacterial Lipopolysaccharides in Mice, II. A Gene that Influences a Membrane Component Involved in the Activation of Bone Marrow-derived Lymphocytes by Lipopolysaccharides," *J. Immun.*, vol. 114, pp. 1462-1468 (1975).
Weiner, "The Antimicrobial Activity of the Cathelicidin LL37 is Inhibited by F-actin Bundles and Restored by Gelsolin," (*Am. J. Respir. Cell Mol. Biol.* vol. 28, pp. 738-745, 2003).
Wen et al., "The Plasma and Cytoplasmic Forms of Human Gelsolin Differ in Disulfide Structure," *Biochemistry*, vol. 35, pp. 9700-9709 (1996).
Yamamura et al., "Sphingosine-1-phosphate inhibits actin nucleation and pseudopodium formation to control cell motility of mouse melanoma cells," *FEBS Letters*, vol. 382, pp. 193-197.
Yatomi, Y., "Sphingosine 1-Phosphate in Vascular Biology: Possible Therapeutic Strategies to Control Vascular Diseases," *Current Pharma. Design*, vol. 12, pp. 575-587, (2006).
Martel, Bronchopneumonia: Causes, Symptoms & Diagnosis. Healthline. Medically reviewed by George Krucik, M.D. Published Jul. 12, 2012. http://www.healthline.com/health/bronchopneumonia#Overview1.
Yang et al., Plasma Gelsolin Improves Lung Host Defense against Pneumonia by Enhancing Macrophage NOS3 Function. Am J Physiol Lung Cell Mol Physiol. May 8, 2015. doi:10.1152/ajplung.00094.2015.
Kucan et al., Influence of topical steroids on bacterial proliferation in the burn wound. J Surg Res. Feb. 1978;24(2):79-82.
Rooney et al., Interleukin 1 beta in synovial fluid is related to local disease activity in rheumatoid arthritis. Rheumatol Int. 1990;10(5):217-9.
Angus et al., "Epidemiology of sepsis: An update," *Crit. Care. Med.*, vol. 29, No. 78 (Suppl.) 2001, pp. S109-S116.
Maury, "Homozygous familial amyloidosis, Finnish type: demonstration of glomerular gelsolin-derived amyloid and non-amyloid tubular gelsolin" In: Clin Nephrol Jul. 1993, vol. 40, No. 1 pp. 53-56 (Abstract Only).
Moss, M., "Epidemiology of Sepsis: Race, Sex, and Chronic Alcohol Abuse," Supplement Article, Clinical infectious diseases: an official publication of the Infectious Diseases Society of America), vol. 41, Suppl. 7, 2005, pp. S490-S497.
Mounzer et al. "Relationship of Admission Plasma Gelsolin Levels to Clinical Outcomes in Patients after Major Trauma" In: Amer. Jour. Resp. Crit. Med. Care Nov. 1999, vol. 160, No. 5 pp. 1673-1681.
Visappaa et al. "Correlation of Ki-67 and gelsolin expression to clinical outcome in renal clear cell carcinoma" In: Urology Apr. 2003, vol. 61, No. 4 pp. 845-850.
Yancey, M.K., et al., "Risk Factors for Neonatal Sepsis," *Obstetrics & Gynecology*, vol. 87, No. 2, 1996, pp. 188-194.
EP 10185573.2, May 16, 2012, Extended European Search Report.
EP 13186249.2, Feb. 17, 2014, Extended European Search Report.
U.S. Appl. No. 13/861,578, filed Apr. 12, 2013, Stossel et al.
U.S. Appl. No. 13/455,878, filed Apr. 25, 2012, Stossel et al.
[No Author Listed] Choice of Control Group and Related Issues in Clinical Trials, E10. ICH Harmonised Tripartite Guideline. International Conference on Harmonisation of Technical Requirements for Registration of Pharmaceuticals for Human Use. Jul. 20, 2000. 35 pages.
[No Author Listed] E10 Choice of Control Group and Related Issues in Clinical Trials. Guidance for Industry. U.S. Department of Health and Human Services, Food and Drug Administration, Center for Drug Evaluation and Research (CDER), and Center for Biologics Evaluation and Research (CBER). May 2001. 37 pages.
[No Author Listed] Pharmacokinetics in Patients with Impaired Hepatic Function: Study Design, Data Analysis, and Impact on Dosing and Labeling. Guidance for Industry. U.S. Department of Health and Human Services, Food and Drug Administration, Center for Drug Evaluation and Research (CDER), and Center for Biologics Evaluation and Research (CBER). May 2003. 19 pages.
Matthay et al., Acute lung injury and the acute respiratory distress syndrome: four decades of inquiry into pathogenesis and rational management. Am J Respir Cell Mol Biol. Oct. 2005;33(4):319-27.

\* cited by examiner

FIG. 3A
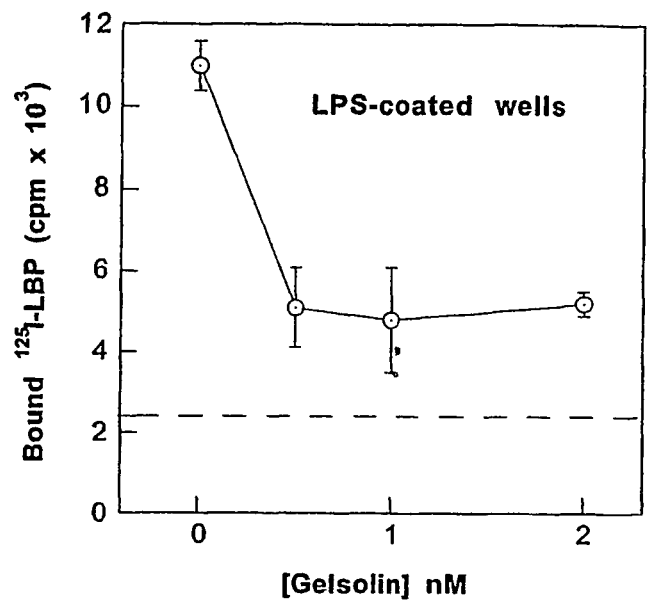
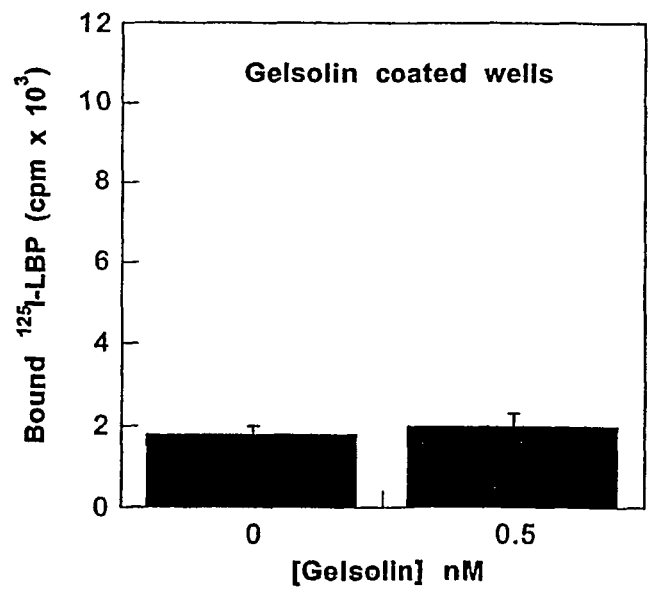
FIG. 3B

FIG. 4A
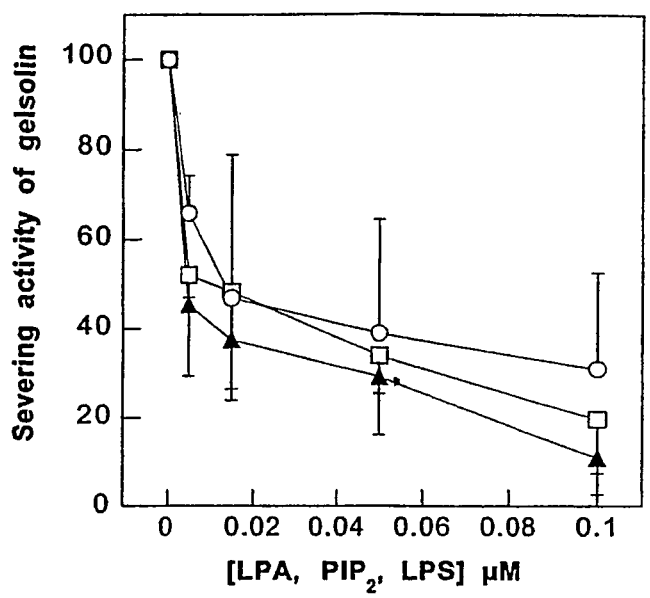
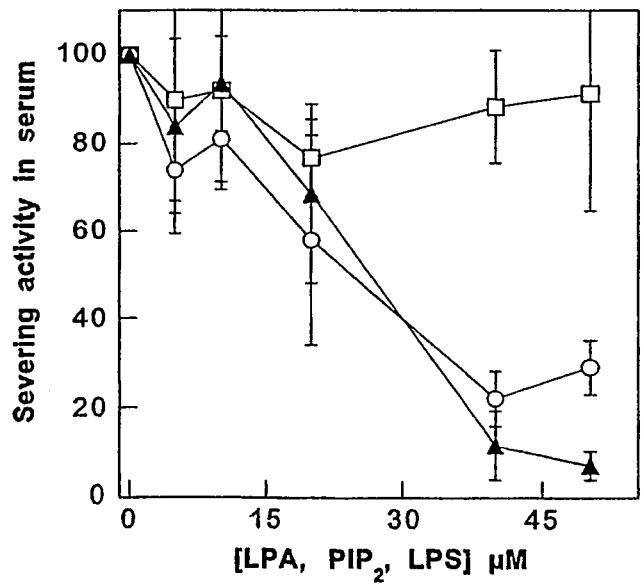
FIG. 4B

METHODS OF USING GELSOLIN TO TREAT OR PREVENT BACTERIAL SEPSIS

REFERENCE TO RELATED APPLICATIONS

This application is filed as a continuation-in-part application of U.S. Ser. No. 10/574,034 filed May 2, 2007, which is a National Phase filing of PCT application PCT/US04/037763, filed on Nov. 12, 2004, and claiming priority to 60/519,286, filed Nov. 12, 2003, each of which is herein incorporated in its entirety.

GOVERNMENT INTERESTS

This invention was supported in part by the National Institutes of Health Grant Nos. grants AR38910 and HL67286. The Government may have certain rights in this invention.

FIELD OF THE INVENTION

The present invention relates to a method of treating, preventing or neutralizing septic shock in mammals.

BACKGROUND OF THE INVENTION

Septic shock from bacterial endotoxins, triggered by release of lipopolysaccharide (LPS) molecules from the outer wall of gram-negative bacteria, is a major cause of human death for which there has previously been no effective treatment once the complex inflammatory pathways have been activated. Delivery of LPS from external fluids to the cell membrane, and ultimately to the LPS receptors is complex, involving a number of external proteins and other factors (Erridge et al., *Microbes Infect.* 4:837-851 (2002); Bosshart et al., *FEBS Lett.* 553:135-140 (2003); Thomas et al., *Biochem. Biophys. Res. Commun.* 307:133-138 (2003); Rustici et al., (1993) *Science* 259, 361-365 (1993)). A critical factor in LPS toxicity is the aggregation-state of this amphipathic molecule, e.g., when LPS are packed into lamellar phases toxicity is low, but high when present in non-lamellar phases (Brandenburg et al. *Carbohydr. Res.* 338:2477-2489 (2003)). As a result, strategies to counteract LPS in serum or cerebrospinal fluid have involved several types of small molecules and proteins, including anti-LPS antibodies, such as transferrin, alpha 2-macroglobulin, Gc-globulin (Berger et al., *Clin. Chim. Acta* 163:289-299 (1987); Berer et al., *Eur. J. Clin. Invest.* 20:66-71 (1990)) and MD-2 (Shimazu et al., *J. Exp. Med.* 189:1777-1782 (1999)).

Lipoprotein particles, such as LPS-binding protein (LBP) are also ligands for LPS (Wright et al., *J. Exp. Med.* 170:1231-1241 (1989)), in which case a rise in plasma lipid levels during sepsis may be a protective response since LPS bound to other molecules appears to lose its stimulatory effect on cells (Casas et al., *J. Surg. Res.* 59:544-552 (1995); Bannerman et al., *J. Dairy Sci.* 86:3128-3137 (2003)), and promotes cytokine tolerance in hepatocytes (Harris et al., *J. Endotoxin Res.* 9:45-50 (2003)). Both LBP and CD14 promote partitioning of LPS into lipoprotein complexes (Vreugdenhil et al., *J. Immunol.* 170:1399-1405 (2003); Wurfel et al., *J. Exp. Med.* 181:1743-1754 (1995)). More importantly, low concentrations of LBP have been shown to enhance the LPS-induced activation of mononuclear cells, whereas increased LBP concentrations inhibit LPS-induced cell stimulation (Gutsmann et al., *Infect. Immun.* 69:6942-6950 (2001)). LBP also delivers LPS to its receptors at the cell membrane. This dual effect of the protein on LPS function reinforces the importance of the lipid aggregation-state, and confirms that toxicity does not result from mass concentration alone. Related to this effect may be the finding that low doses of antimicrobial agents can lead to exacerbation of the toxicity associated with LPS (Tauber et al., *J. Infect. Dis.* 156:456-462 (1987); Mertsola et al., *Pediatr. Infect. Dis. J.* 8:904-906 (1986)).

Lipoteichoic acid (LTA) is a surface-associated adhesion amphiphile found in the cell walls of most gram-positive bacteria, and acts as a regulator of autolytic wall enzymes (muramidases). The toxin is released from the gram-positive bacterial cells, mainly after bacteriolysis induced by lysozyme, cationic peptides from leucocytes, or beta-lactam antibiotics or leukocytic mediators, and plays an important role both in the colonization of bacteria and the consequent release of cytotoxic mediators in colonized organs. LTA binds non-specifically to membrane phospholipids in target cells, or it binds specifically to CD14 and to Toll-like receptors (TLRs). When LTA is bound to a target, it can interact with circulating antibodies and activate the complement cascade to induce a passive immune kill phenomenon (Hummell et al., *J. Clin. Invest.* 77(5):1533-1538 (1986)), and it triggers numerous events associated with sepsis, including the respiratory burst and the release by neutrophils and macrophages of reactive oxygen and nitrogen species, acid hydrolases, arachidonic acid metabolites, highly cationic proteinases, bactericidal cationic peptides, growth factors, stimulators of chemotaxis and phagocytosis, and cytotoxic cytokines, including tumor necrosis factor (TNF), interleukin-1 (IL-1), inflammatory chemokines, such as IL-8, and platelet-activating factor (PAF). The cytokines then bind to cytokine receptors on target cells and initiate inflammation, as well as activating both the complement pathways and the coagulation pathway, in a manner similar to endotoxin (LPS) from gram-negative cell walls, and in fact, may act in synergy to amplify cell damage. Consequently, innate immune defenses, such as the inflammatory response, the complement pathways, and the coagulation pathway become harmful to the body when there is an excessive production of cytokines. LTA also inhibits platelet aggregation, which may contribute in part to bleeding diathesis, which is a characteristic response in gram-positive septicemic patients. Thus, LTA shares many pathogenetic properties with LPS endotoxins.

In animal studies, LTA has been reported to induce arthritis, nephritis, uveitis, encephalomyelitis, meningeal inflammation, and periodontal lesions, and also to trigger cascades resulting in septic shock and multi-organ failure. However, LTA binding to targets can be inhibited by antibodies, phospholipids, and specific antibodies to CD14 and TLR. In vitro, the release of LTA can be inhibited by non-bacteriolytic antibiotics, and by polysulphates, such as heparin, that apparently interfere with the activation of autolysis.

Thus, evidence has shown that LTA is a significant virulence factor in infectious and post-infectious sequelae caused by gram-positive bacteria, making the development of effective anti-bacteriolytic drugs and multi-drug strategies to attenuate LTA-induced secretion of pro-inflammatory agonists of great importance to combat septic shock and multi-organ failure. Moreover, gram-positive and gram-negative infections often co-exist, producing a synergistic effect of LPS and LTA, and results in a clinical septicemia of greater severity than infection by either pathogen alone. Thus, LTA sits at the heart of septicemia and blockade of its binding could confer significant clinical activity.

Naturally occurring amphiphilic lysosphingolipid molecules control vital functions of the cell through their interaction with specific receptors to modulate a variety of signaling pathways. Proliferation, differentiation and programmed death result from a fine balance of signals, among which sphingosine and structurally related molecules play fundamental roles, acting as either first or second messengers. Sphingosylphosphocholine (SPC) is a deacylated derivative of sphingomyelin, which is known to accumulate in Niemann-Pick disease type A.

Sphingosine-1-phosphate (S1P) is an important cellular metabolite, derived from ceramide that is synthesized de novo or as part of the sphingomyelin cycle (in animal cells). In plasma, it can reach a concentration of 0.2 to 0.9 µM, and is found in association with the lipoproteins, especially the HDL (Goetzl et al, *J. Biol. Chem.* 275(19):14573-14578 (2000)). It has also been found in insects, yeasts and plants.

S1P is a highly active cellular growth factors that is generated enzymatically from cellular membrane precursors and secreted by activated platelets, leukocytes, epithelial cells, and some types of tumors. S1P is stored in relatively high concentrations in human platelets, which lack the enzymes responsible for its catabolism, and it is released into the blood stream upon activation by physiological stimuli, such as growth factors, cytokines, and receptor agonists and antigens. It may have a critical role in platelet aggregation and thrombosis and could aggravate cardiovascular disease. On the other hand, the relatively high concentration of the metabolite in high-density lipoproteins (HDL) may have beneficial implications for atherogenesis. For example, reportedly S1P together with other lysolipids, such as SPC and lysosulfatide, may be responsible for the beneficial clinical effects of HDL by stimulating the production of the potent antiatherogenic signaling molecule nitric oxide by the vascular endothelium. In addition, S1P functions intracellularly to regulate calcium mobilization and cell growth in response to a variety of extracellular stimuli. However, Yamamura et al., *FEBS Lett.* 382: 193-197 (1996) dismissed the speculation that S1P could physically interact with actin-binding proteins, demonstrating that S1P was poorly active and yielded only a maximal dissociation of 10%.

Gelsolin is a normal serum protein, but unlike other mammalian proteins, gelsolin has both cytoplasmic and secreted isoforms derived by alternative slicing of the message from a single gene (Sun et al., *J. Biol. Chem.* 274:33179-33182 (1999)). Although originally identified as a cellular protein, cytoplasmic gelsolin also exists as an abundant secreted isoform of nearly identical structure and is a product of the same gene (Kwiatkowski et al., *Nature* 323:455-458 (1986)). It has a six-fold sequence repeat structure that is highly conserved among gelsolins of vertebrate species, and that is characteristic of a large family of gelsolin-related proteins (Kwiatkowski, *Curr. Opin. Cell Biol.* 11:103-108 (1999)).

Secretory gelsolin, now called "plasma gelsolin," circulates in human and rodent blood at concentrations of 250±50 µg/L (Lind et al., *Am. Rev. Respir. Dis.* 138:429-434 (1988)). Plasma gelsolin has a processed signal sequence, but is otherwise identical to the cellular form, with the exception of a 23 amino acid stretch at the amino terminus of the molecule, designated the "plasma extension." Therefore, the plasma form of gelsolin is slightly larger (84 kDa), than the cellular variant (82 kDa). Recombinant human gelsolin (rhGSN) (Biogen IDEC, Inc., Cambridge, Mass.) is produced in *E. coli*, and though it has the same primary structure as native protein, under standard conditions of purification, it differs from natural human plasma gelsolin by a disulfide bond that is present in the natural protein. The recombinant protein is, therefore, properly oxidized after purification, and its structure and functions are indistinguishable from purified human plasma gelsolin (see, Wen et al., *Biochemistry* 35:9700-9709 (1996)).

Although secreted by many tissues, the major source of human plasma gelsolin is striated muscle (Kwiatkowski et al., *J. Biol. Chem.* 263:8239-8243 (1988)). This form of gelsolin appears to be distributed throughout extracellular fluids and has a typical residence time in plasma (Lind et al., *J. Clin. Invest.* 78:736-742 (1986)). It is not modified post-translationally by glycosylation or other reactions, nor is it an acute phase reactant. In fact, little information exists concerning its function or regulation of its production. For example, gelsolin did not bind S1P, nor did it deliver S1P to rat cardiac myocytes (Goetzl et al., supra, 2000). However, it is known that levels of gelsolin drop in clinical settings when inflammation or sepsis occurs, i.e., tissue injury associated with breakdown of membrane barriers and exposure of actin to the extracellular environment results in reductions in plasma gelsolin levels (Lee et al., *N. Engl J. Med* 326:1335-1341 (1992)).

As a result, plasma gelsolin depletion precedes and predicts complications of severe injury, such as respiratory failure and death in animals including humans (Mounzer et al., *Am J. Respir. Crit. Care Med.* 160:1673-1681 (1999); DiNubile et al., *Blood* 100:4367-4371 (2002)). For example, a drop in plasma gelsolin levels to <50% normally is a strong predictor of adverse clinical outcomes associated with massive inflammation, although neither a causative role, nor a treatment has been identified based on this finding (Dahl et al., *Shock* 12:102-104 (1999); Dahl et al., *Crit. Care Med.* 31:152-156 (2003); Lind et al., 1988, supra; Smith et al., *Blood* 72:214-218 (1988); Suhler et al., *Crit. Care Med.* 25:594-598 (1997)). However, replacement of depleted plasma gelsolin levels has attenuated the pathologic sequelae of severe primary injuries in animal models (Christofidou-Solomidou et al., *J. Investig. Med.* 50: 54-60 (2002); Rothenbach et al., *J. Appl. Physiol.* 96:25-31 (January 2004)), supporting the findings of the present invention.

In response to acute trauma and/or infection, abundant but normally intracellular G-actin (monomeric actin) is released into extracellular spaces from damaged or dying cells and tissues and circulates in fluid and blood. Once released, G-actin has a strong tendency to polymerize to F-actin. The persistance of filaments of F-actin in the microvasculature of mammals can result in venous obstruction, pulmonary microthrombii and/or endothelial injury, and induces or enhances platelet agglutination in the blood, thereby triggering thrombus development (Scarborough et al., *Biochem. Biophys. Res. Commun.* 100:1314-1319 (1981)). Combined, these effects alter the characteristics of normal vascular flow in mammals, and in turn, can result in actin toxicity disorders and contribute to the pathogenesis of organ injury at sites removed from the primary insult (Dahl et al., *Crit. Care Med.* 26:285-289 (1998); Lee et al., 1992, supra; Mounzer et al., 1999, supra, see also U.S. Pat. No. 5,593,964).

However, various actin-regulating proteins contribute to the reversible conversion of filaments ("gel") and monomers (liquid "sol"), and changes occur depending on extracellular stimuli (see, U.S. Pat. No. 6,271,353). Plasma gelsolin and secreted Gc-globulin act in a coordinated manner, representing an "actin-scavenger system," to depolymerize and remove the actin filaments released from damaged cells. Gelsolin binds to both monomeric and filamentous actin (Yin et al., *Nature* 281:583-586 (1979); Yin et al., *NJ. Biol. Chem.* 259: 5271-5276 (1984)), although following injury, gelsolin preferably binds to and severs the actin filaments to promote rapid depolymerization (Sun et al, 1999, supra), whereas Gc-globulin binds to the actin monomers to shift the actin monomer/polymer equilibrium back toward depolymerizations and prevent repolymerization (Goldschmidt-Clermont et al., *J. Clin. Invest.* 81:1519-1527 (1988)).

This binding requires the presence of micromolar concentrations of calcium ($Ca^{2+}$), which may include added calcium or endogenously available $Ca^{2+}$ in the patient. Moreover the binding is very tight, having a dissociation constant in the nanomolar range. In fact, when gelsolin binds actin filaments in the presence of calcium, it ruptures or severs the filaments at the binding site by breaking the noncovalent bonds holding actin monomers together within the polymer (Janmey et al., *Biochemistry* 24:3714-3723 (1985)). Following the actin severing reaction, gelsolin remains tightly bound to one end of the polarized actin filament, the end conventionally defined as "barbed." This is also the end that rapidly exchanges monomers.

Removing calcium by chelation does not dissociate gelsolin from the barbed ends of the actin filaments. Instead, phosphoinositides (also referred to as phosphorylated inositol phospholipids, or "PPIs"), which are important signal transduction intermediates, effect this separation at the plasma membrane. Gelsolin binds with high affinity and selectivity to PPI and to lysophosphatidic acid (LPA) (Janmey et al., *J. Biol. Chem.* 262:12228-12236 (1987); Meerschaert et al., *Embo J.* 17:5923-32 (1998)). PPIs, therefore, regulate the intracellular actin-binding function of gelsolin, leading to the hypothesis that a reciprocal relationship, between calcium transients and membrane phosphoinositide synthesis and degradation, regulates gelsolin and cellular actin remodeling responses (Stossel, *J. Biol. Chem.* 264, 18261-18264 (1989)). Gelsolin binding to LPA, modulates its receptor-mediated biological effects, leading to the belief that it may act as a carrier of LPA to some cellular receptors, and buffers bioactive inflammatory lipid mediators (Goetzl et al., supra, 2000).

Calcium and phosphoinositides also control the actin-binding functions of plasma gelsolin in vitro (Janmey et al., *Chem. Biol.* 5:R81-85 (1998)). The PPI regulatory site of gelsolin resides within a 20 residue linear sequence that connects the first and second folded domains of the protein. Biochemical and mutational studies have implicated 10 strategically organized basic and hydrophobic amino acids (160-169, SEQ ID No:1 QRLFQVKGRR) in the 684-residue plasma gelsolin molecule that accommodate tight binding to the negatively-charged phosphomonoesters and hydrophobic acyl chains of anionic phospholipids (Janmey et al., *J. Biol. Chem.* 267:11818-11823 (1992). Synthetic peptides of this sequence have a PPI binding affinity similar to that of intact gelsolin (Id).

The methods used to measure the function of gelsolin, have exploited gelsolin's calcium-dependent actin filament severing function, or actin monomer nucleation activities, or the actual mass of gelsolin, using western blotting or immunochemical (usually ELISA) assays. The assays used to quantify gelsolin have relative advantages and disadvantages. For example, the assays measure only severing activity that is directly measurable by fluorimetry (Janmey et al., *Blood* 70:524-530 (1987)) and the assays are specific for free gelsolin, but actin and lipid binding to gelsolin inhibit this function. Nucleation activity and the structural assays do not differentiate free from complexed gelsolin. However, different assays have thus far yielded very similar results for plasma gelsolin levels in control samples, and generally consistent degrees of diminution in plasmas from injured animals or humans, with the exception that severing activity is lower than expected. However, there are also unexplained data from studies showing diminished severing, but not total gelsolin activity in serum samples with no evidence of actin, suggesting that another ligand may have bound the gelsolin.

While there is no apparent relation between the function or metabolism of LPS and either LPA or PIP2 (phosphatidylinositol-4,5-bisphosphate), these lipids share two unusual and essential structural characteristics, and as acidic lipids, they superficially resemble LPS in that all have phosphomonoesters juxtaposed to a hydrophobic interface (Erridge et al., 2002, supra). The active site of each molecule contains a phosphomonoester emanating from a carbohydrate base, glycerol in the case of LPA, and a sugar ring for LPS and PIP2. These moieties, which are present in few other lipids, present possibilities for electrostatic and hydrogen-binding interactions that stabilize both lipid-protein and lipid-lipid complexes ((Liepina et al., *Biopolymers* 71:49-70 (2003)). Also, none of these lipids forms lamellar phases by itself (e.g., Flanagan et al., *Biophys. J.* 73:1440-1447 (1997)), LPA and PIP2 binding to gelsolin appears to be strongest when the lipid is in micelles or putative lipid clusters within bilayer vesicles (Meerschaert et al., *Embo J.* 17:5923-5932 (1998); Tuominen et al., *Eur. J. Biochem.* 263:85-92 (1999); Janmey et al., *J. Biol. Chem.* 262:12228-12236 (1987)).

Plasma gelsolin depletion contributes to the pathophysiology of pulmonary microvascular dysfunction resulting from a primary burn- or bacterially-induced inflammation, and inflammation-induced lung injury (Rothenbach et al., 2004, supra). A blatant clinical example of secondary tissue injury associated with, and resulting from, a depletion of gelsolin, is adult respiratory distress—multiple organ dysfunction syndrome (ARDS/MODS) (Ware et al., *N. Engl. J Med.* 342: 1334 (2000)). Plasma gelsolin levels have dropped to reportedly, on average, 30% of normal values in established ARDS cases (Yin et al, 1979, supra). An unimpressive track record of pharmacologic interventions in established ARDS, suggests that once full-blown ARDS occurs, it may no longer be possible to inhibit the broad spectrum of activated inflammatory mediators that are involved.

Accordingly, at the present time, there is no agent to clinically neutralize endotoxins, or prevent or avert the resulting bacterial sepsis, and often death. A need has remained, therefore, until the present invention, to better understand PPI-binding proteins and the lipid ligands of these proteins, how they affect the function of gelsolin, how altering PPI levels in the body works to reorganize the actin cytoskeleton, and the role of these lipids and lipid binding proteins, such as gelsolin, in inflammation, particularly with regard to developing methods for treating, alleviating, or even preventing, the onset and pathology of bacterially-caused endotoxemia, sepsis, inflammation-induced pulmonary microvascular dysfunction following severe burns or myocardial infarction, ARDS or cystic fibrosis.

SUMMARY OF THE INVENTION

Gelsolin-depletion contributes to the pathophysiology of microvascular dysfunction during inflammation in trauma and burn patients, as well as, in septic shock resulting from bacterial endotoxins, triggered by release of lipopolysaccharide (LPS) molecules from infecting gram-negative bacteria, and by lipoteichoic acid (LTA) from infecting gram-positive bacteria. As a result, the present invention provides methods to counteract the decreasing plasma gelsolin levels at a sufficiently early time point in inflammation-induced injury by the infusion of gelsolin, that microvascular dysfunction is averted. In fact, in accordance with preferred embodiments of the invention, intravenous infusion of synthetic, recombinant human gelsolin (recombinant replacement therapy) completely prevented the irreversible tissue damage and increased microvascular permeability otherwise associated with bacterial endotoxin production, and death. Thus, the invention provides important new evidence to support the finding that circulating gelsolin has an important protective function against the pathophysiology of systemic inflammation.

It is an object of the present invention is to provide a method for increasing the concentration of gelsolin or functionally equivalent peptide fragment thereof, in blood or extracellular fluid of a patient in vitro or in vivo, wherein such increased concentration of gelsolin is needed, said method comprising administering to the patient a therapeutically effective amount of gelsolin, or functionally equivalent peptide fragment thereof.

It is a further object to provide methods for decreasing the concentration of bacterial LPS or LTA in blood or extracellular fluid of a patient, thereby preventing, neutralizing or reducing endotoxemia or endotoxin-induced septic shock in a patient in vitro or in vivo, wherein the patient is subject to or susceptible to bacterial infection, said method comprising administering a therapeutically effective amount of gelsolin, or functionally equivalent peptide fragment thereof, to decrease the concentration of bacterial LPS or LTA and protect the patient from endotoxemia or endotoxin-induced sepsis. Consequently, the method further blocks, reduces or ameliorates bacterial LPS- or LTA-induced disruption of mammalian cellular responses or formation of toxic structures in vitro or in vivo. It also blocks, reduces or ameliorates the inhibition of fibrinolysis by excess, extracellular free actin in blood or extracellular fluid of a patient in vitro or in vivo. In addition it restores or maintains normal aggregation of platelets in a patient, wherein the patient is subject to or susceptible to LPS- or LTA-induced generalized coagulation dysfunction.

It is an additional object that each embodied method be useful in vitro or in the actual gelsolin replacement therapy of a patient.

When such methods are used in vivo, it is a further object that the method effectively inhibits, ameliorates or prevents secondary tissue injury in the patient resulting from an accumulation of excess bacterial LPS or LTA, said method comprising administering a therapeutically effective amount of gelsolin, or functionally equivalent peptide fragment thereof. Moreover, the methods are effective even when the secondary tissue injury in the patient is remote from the site of primary infection or trauma.

It is yet another object to provide method for predicting adverse clinical outcome associated with massive inflammation in a patient susceptible to inflammatory shock or endotoxin-induced sepsis, said method comprising measuring the circulating gelsolin concentration in the patient, wherein a decrease ≤30% of normal, pre-trauma or pre-infection gelsolin levels predicts such adverse outcome and predicts a need for gelsolin therapy. Also provided are the compositions of gelsolin or active fragment thereof as used in the foregoing methods.

Additional objects, advantages and novel features of the invention will be set forth in part in the description, examples and figures which follow, all of which are intended to be for illustrative purposes only, and not intended in any way to limit the invention, and in part will become apparent to those skilled in the art on examination of the following, or may be learned by practice of the invention.

BRIEF DESCRIPTION OF THE FIGURES

The foregoing summary, as well as the following detailed description of the invention, will be better understood when read in conjunction with the appended drawings. It should be understood, however, that the invention is not limited to the precise arrangements and instrumentalities shown.

FIG. 1A shows the binding of $^3$H-labeled LPS to PBP10 peptides±cold LPS (PBP10 shown by open circles; PBP10+LPS shown by open squares; rhodamine-B (RhB)-labeled QRL fragment±LPS shown by filled circles). FIG. 1B shows the optical density (OD) of gelsolin in solutions containing varying amounts of LPS (open circles) or LPA (open triangles) or PS (filled triangles). FIG. 1C shows rhodamine-B fluorescent changes of PBP10-peptide in the presence of different lipids or controls (PS, open circles; PIP2, closed squares; LPS, open circles; LPS+PIP2, closed circles; LPA, open triangles). FIG. 1D shows the fluorescence emission spectra of pyrene-SEQ ID No:1 (open circles) in the presence of LPS from E. coli (peptide+LPS; open triangles), PIP2 (peptide+PIP2; filled inverted triangles) and LPA (peptide+LPA; filled triangles). Data shown in FIGS. 1A, 1B and 1C are means±SD of 2-4 experiments; FIG. 1D data are representative for three independent experiments.

FIGS. 3A and 3B graphically show that gelsolin competes with and inhibits the binding of LPS-binding protein, LBP, from binding to LPS. FIG. 3A shows $^{125}$I-LBP does not bind to LPS coated wells that had been previously incubated with gelsolin; but gelsolin does not interact directly with the LBP (FIG. 3B). Data shown are mean±SD of 4 experiments.

FIGS. 4A and 4B graphically show the effect of LPA (squares), PIP2 (circles) and LPS from E. coli (triangles) on actin filament severing activity of recombinant human gelsolin (rhGLS) (FIG. 4A), or human blood plasma (FIG. 4B). Severing activity was determined from the rate of decreased fluorescence during depolymerization following the addition of rhGLS or blood plasma to an F-actin solution polymerized with 50% pyrene labeled G-actin. Data shown are mean±SD of 4 to 6 experiments.

FIG. 7A shows that LTA inhibits gelsolin's (50 nM) actin severing activity nearly as well as LPS does. FIG. 7B shows that LTA binds to the gelsolin peptide PBP10 (10 µM)

as judged by changes in PBP10 fluorescence with approximately the same efficiency as PIP2.

Figure 8:
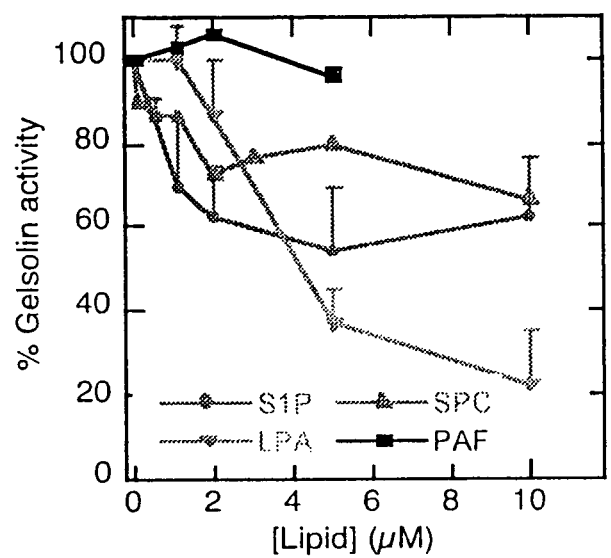

FIG. 8 shows that gelsolin prevents LTA activation of human aortic endothelial cells (HAEC). The addition of LTA stimulated binding of labeled neutrophils to the endothelial surface, but when physiological concentrations of gelsolin were added along with LTA, neutrophil adhesion is reduced to near baseline values.

Figure 9:
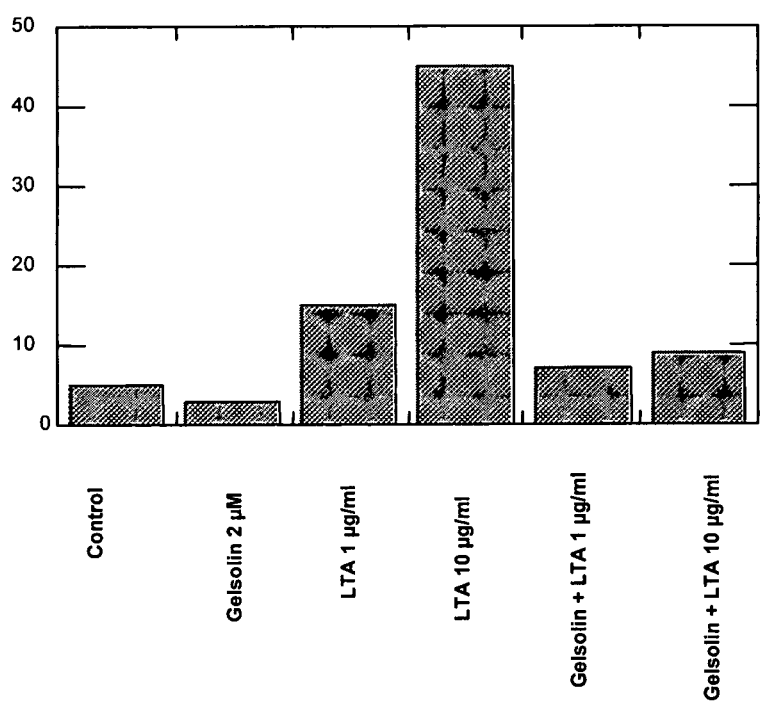

FIG. 9 graphically depicts interactions of bioactive eukaryotic lysolipids with gelsolin, showing that the lysophospholipids inhibit gelsolin (50 nM) to variable extents.

DETAILED DESCRIPTION OF CERTAIN EMBODIMENTS OF THE INVENTION

The present invention provides methods for effectively using plasma gelsolin, or active fragments, homologs or analogs thereof, to treat, neutralize, prevent or otherwise control septic shock in a patient, resulting from endotoxins, triggered by release of lipopolysaccharide (LPS) molecules from infecting gram-negative bacteria. Also the invention provides methods for effectively using plasma gelsolin, or active fragments, homologs or analogs thereof, to treat, neutralize, prevent or otherwise control septic shock in a patient, resulting from endotoxins, triggered by release of bacterial lipid lipoteichoic acid (LTA) from gram positive bacteria. In addition, the invention further provides methods for effectively using plasma gelsolin, or active fragments, homologs or analogs thereof, to treat, neutralize, prevent or otherwise control septic shock in a patient, resulting from sepsis-relevant eukaryotic signaling lysolipids sphingosine phosphate (S1P) and sphingosine phosphocholine (SPC). As a result, methods are provided to counteract or prevent sepsis, severe inflammation, or other conditions, such as inflammation-induced pulmonary microvascular dysfunction, associated with a marked decrease in plasma gelsolin levels in the patient by modulating LPS, LTA, S1P and/or SPC.

In vitro and in vivo evidence, including solid phase binding assays, fluorescence, absorbance measurements, and functional assays of actin depolymerizing effects, demonstrate a clear interaction between LPS, LTA, S1P or SPC and gelsolin, and show that gelsolin binds with approximately equal strength individually to LPS and LTA, and that it binds more tightly to LPS and LTA, respectively, than it does to its other known lipid ligands, e.g., phosphatidylinositol 4,5 bisphosphate (PIP2) and lysophosphatidic acid (LPA). LTA, LPS and PIP2 all appear to bind to one common site within gelsolin. See, e.g., Mintzer et al. *Biochim. Biophys. Acta*. in press (2006).

The tight and selective binding of gelsolin to LPS, LTA, S1P and SPC, respectively has several implications for the function of plasma gelsolin, and the invention, therefore, offers methods to counteract the toxic effects of these bioactive lipids. Despite a strong clinical correlation between markedly lowered gelsolin levels and susceptibility to inflammatory shock, until the present invention there had been no demonstration or explanation of a therapeutic utility of the interaction between human plasma gelsolin and bacterial LPS that inactivates both the actin scavenging function of gelsolin and the cytotoxic effect of LPS. The current findings indicate that LPS and LTA, in addition to LPA and actin, may be the harmful agent responsible for pathologies following trauma, burns or bacterial infection that leads to gelsolin depletion.

LTA shares many of its pathogenetic properties with endotoxins (lipopolysaccharide). In animals, LTA is known to have induced uveitis, encephalomyelitis, meningeal inflammation, and periodontal lesions. It also triggers cascades resulting in septic shock and multi-organ failure (Ginsburg, Lancet Infect. Dis. 2(3):171-9 (2002)). In sepsis, gram-positive and gram-negative bacteria provoke similar inflammatory processes. Lipopolysaccharides represent the principal immunostimulatory components of gram-negative bacteria, whereas lipoteichoic acid appears to be the major immuno-stimulatory molecule of the gram-positive cell wall. LTA is a potent activator of cytokine generation in human neutrophils (Hattar et al., Crit. Care Med. 34:835-841 (2006)), and of the production of TNF-alpha and IL-6 in Kupffer cells (Gunhild, *Surg. Infect.* 4(2):181-189 (2003)). LTA also causes significant up-regulation of the surface expression of ICAM-1 and receptors involved in antigen presentation (HLA-DR) on whole blood monocytes, similar to that obtained with LPS (Jorgensen et al., *Clin. Diagn. Lab. Immunol.* 8:515-521 (2001)). As with LPS, innate immune recognition of LTA requires LBP, CD14, and TLR.

The molecular structure of LPS is heterogeneous, even from a single bacterium, and often is widely variable among different bacteria. Why some forms of LPS are more toxic than others, remains unresolved, but as demonstrated in the examples that follow, not only is the covalent structure of the compound important, but the form of the LPS aggregate appears to be an equally relevant determinant of toxicity. The strong binding of gelsolin to LPS and LTA, as well as to LPA and PIP2, points to the importance of aggregate packing in both the biochemistry and biologic function of protein-lipid interactions. LPS, LTA, LPA, and PIP2 are similar, but not identical. However, they are, in fact, sufficiently different that highly specific lock and key binding interactions cannot explain these effects.

One of proposed mechanisms of LPS deactivation in blood is LBP-mediated incorporation of LPS molecules into blood lipoproteins (Yu et al., *J. Clin. Invest.* 99:315-324 (1997). A previous kinetic study suggests, that LPS-binding protein (LBP), a high affinity carrier for LPS, is one of the first plasma components to interact with Lipid A (Tobias et al., *Infect. And Immun.* 50:73-76 (1985)), thereby influencing interactions of LPS with lipoprotein and cellular targets and serving as an acute phase reactant. It is increased during trauma or infection, which results in increased plasma opsonization capacity (Tobias et al., *J. Exp. Med.* 164:777-793 (1986); Mathison et al., *J. Immunol.* 149:200-206 (1992)). Therefore, the present findings are significant, showing that gelsolin competes with LBP, further disrupting the onset of sepsis. Accordingly, the present invention provides methods for complexing circulating LPS by LPS-binding proteins or lipids, thereby preventing the formation of the toxic structures.

Less is known about the mechanisms by which LTA is delivered to its eukaryotic target cells, as compared to the literature on LPS. However, recent studies show that both LBP and CD14 can bind LTA, and deliver it selectively to Toll-like receptor-2 (TLR-2) in a manner analogous to the trafficking of LPS. For example, LTA from *Streptococcus pneumoniae* and *Staphylococcus aureus* activates immune cells via TLR-2, LBP, and CD 14, whereas TLR-4 and MD-2 are not involved (Schroder et al., *J. Biol. Chem.* 278(18): 15587-15594 (2003)). As a further analogy between LTA and LPS, it has been reported that plasma lipoproteins bind LTA, as well as LPS (van Oosten et al., *J. Endotoxin Res.* 7(5):381-384 (2001)). This similarity strengthens the hypothesis that plasma sequestration and presentation to corresponding cellular receptors is as important for LTA as it is for LPS.

S1P is an important bioactive lipid that can become thrombogenic, and cause or aggravate cardiovascular diseases especially under certain pathological conditions. It is likely that regulation of S1P biological activities is important for the therapeutic purposes, e.g., to control vascular and inflammatory disorders. Binding of gelsolin with S1P may prevents its interaction with S1P receptors (Yatomi, *Curr. Pharm. Des.* 12:575-587 (2006)).

When the term "gelsolin" is used herein, it is herein to mean, whole or intact gelsolin or a biologically active abbreviated sequence forms of gelsolin, and their biologically active analogs (including muteins) having substituted, deleted, elongated, replaced, or otherwise modified sequences which possess LPS-, LTA-, S1P- or SPC-binding bioactivity that is substantially similar to that of native gelsolin, as well as biologically active amino acid sequences substantially similar to gelsolin. As used herein, "biologically active equivalent peptide analogs" refers to "functionally equivalent peptide fragments," including homologs of gelsolin, preferably SEQ ID No:1, that contain conservative amino acid substitutions, provided that the peptide analogs which contain the conservative substitutions bind to a PPI (phosphoinositide) regulating the intracellular actin binding function of gelsolin, and have transport-mediating activity, as determined, for example, in an in vitro screening assay. As used herein, "conservative amino acid substitution" refers to an amino acid substitution, which does not alter the relative charge or size characteristics of the peptide in which the amino acid substitution is made. Moreover, as used herein, the term "gelsolin" is intended to include naturally occurring or recombinant or synthetically produced isolated gelsolin or functionally equivalent peptide fragments thereof. All are included within the present invention.

Gelsolin Interaction with LPS

Turning to the Figures of the present invention, which will be described in greater detail in the Examples that follow, in a preferably embodied solid phase binding assay, $^3$H-LPS bound in a saturable manner to surfaces that were coated with the PIP2-binding peptide SEQ ID No:1 (QRLFQVKGRR; also referred to herein as "PBP10"), but not to surfaces coated with a truncated peptide, QRL, which does not bind PIP2. Addition of a substantial (5-fold) excess of unlabeled LPS reduced that binding to PBP10 by approximately 50%, but it had no effect on the small amount of non-specific binding to the control peptide-treated surface. See FIG. 1A. The finding that a small active peptide fragment of gelsolin, such as PBP10, was as effective as whole gelsolin for binding these lipids while, for example, only the correctly folded protein can bind actin, points to a disclosed general binding of LPS through its lipid-binding domain. Under certain conditions, a functionally equivalent peptide fragment may bind better to LPS than intact gelsolin does, perhaps in settings where steric constraints prevent the whole protein from finding the binding site on LPS, while allowing the smaller peptide to do so.

Binding of LPS to intact gelsolin was evident by a change in UV absorbance (FIG. 1B) of at least 10%, more preferably 20%, more preferably 30%, with a maximal decrease seen of ~35%, although it could be greater. Such a decrease in tyrosine and tryptophan fluorescence, due to decreased absorbance, has been documented as an assay for PIP2 binding to gelsolin (Lind et al., 1997, supra). LPA also diminished gelsolin's absorbance, but PS had no effect. Moreover, binding of PPIs and LPA to gelsolin strongly inhibited gelsolin's actin filament severing function.

Figure 1A:
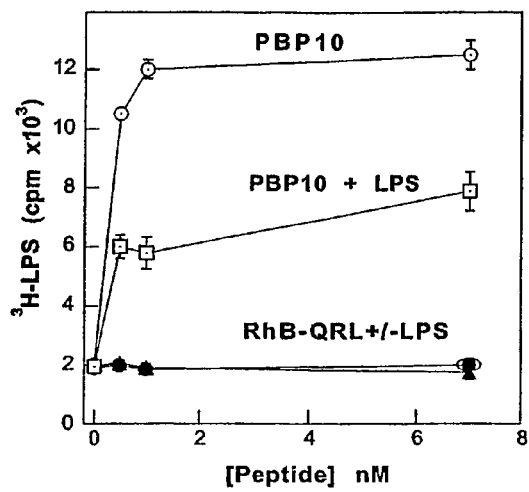
FIGS. 1A-1D graphically depict the interaction of PBP10 and gelsolin with LPS.
Figure 1B:
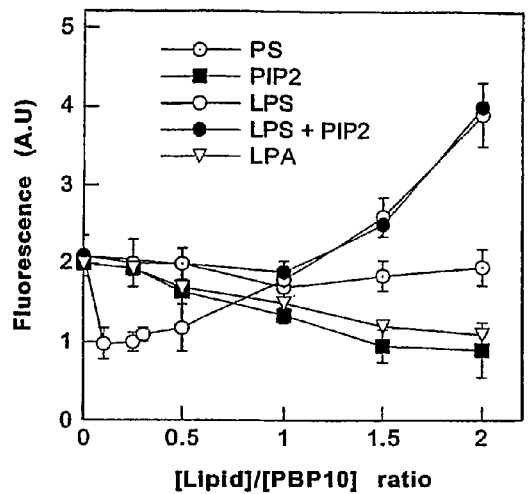
Figure 1C:
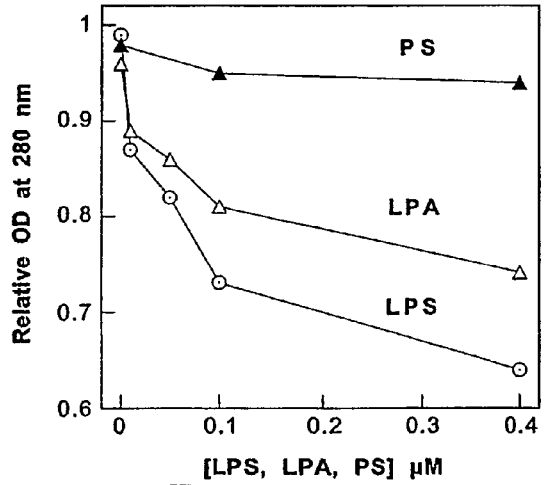

The fluorescence of rhodamine-B-labeled-SEQ ID NO:1 (QRLFQVKGRR) is also changed by LPS, as shown in FIG. 1C. LPS and PIP2, but not phosphatidylserine (PS), induced identical concentration-dependent fluorescence quenching of PBP10. LPS and PIP2 also caused congruent changes in the fluorescent spectrum of pyrene derived SEQ ID No:1 (QRLFQVKGRR), in which binding to these lipids, but not to PS, induces clustering of the peptide with resulting excimer fluorescence of the pyrene group. This was manifest as a large increase in fluorescence emission at 480 nm (data not shown).

After an initial decrease in fluorescence at low LPS to peptide ratios, the peptide fluorescence increases strongly, further suggesting insertion of the peptide-bound rhodamine-B into a more hydrophobic environment. Lipid A (the LPS derivative lacking polysaccharide) causes weaker, but detectable inhibition; whereas anionic lipids, like PS, have no inhibitory effect (data not shown). Thus, LPS is a more potent inhibitor than either LPA or P1P2, yet certain structural similarities between PIP2, LPA and LPS suggest that LPS binds gelsolin at the same site as PIP2 and LPA. When tested, the same types of assays that have documented binding of PPIs and LPA to gelsolin, all show that gelsolin binds LPS at least as strongly, and in some contexts with higher affinity than it binds PIP2, and the binding site is, in fact, localized to apparently to the same region in gelsolin where PIP2 and LPA bind.

Figure 1D:
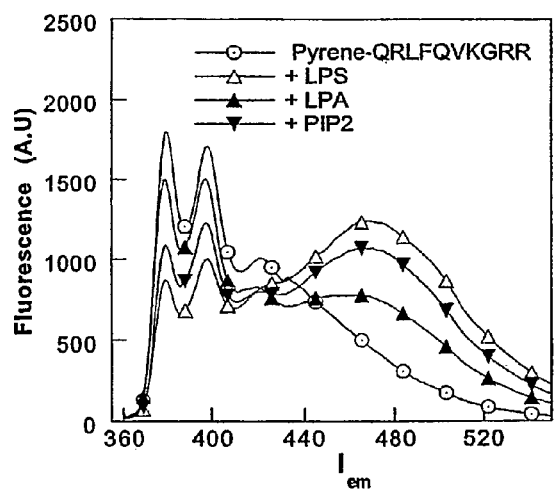

FIG. 1D confirms the rhodamine studies, using a pyrene-derivatized gelsolin peptide, although larger amounts are needed, as compared to inhibition of pure gelsolin in aqueous solution. Binding to LPS induced clustering of the peptide with a resulting excimer fluorescence of the pyrene group, which was evident as a large increase in fluorescence emission at 480 nm. LPS, LPA, and PIP2 had similar abilities to induce excimer formation, whereas PS had no effect (data not shown).

Figure 2:
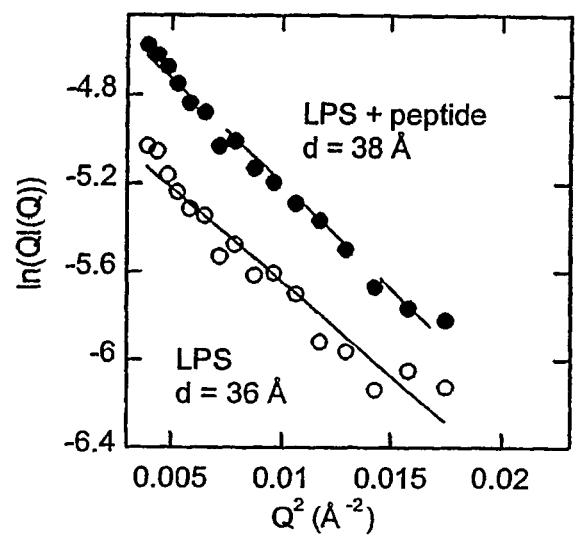
FIG. 2 graphically shows a neutron scattering plot of the molecular structure of LPS+gelsolin SEQ ID No:1.

The molecular structure of LPS and its complexes with proteins, such as gelsolin can be further defined by plotting neutron scattering intensity. For example, the neutron scattering intensity of LPS+SEQ ID No:1 (gelsolin peptide residues 160-169) is shown in FIG. 2. The linearity of the plot suggests that LPS forms a cylindrical structure, but that the addition of gelsolin alters the diameter of LPS, confirming that neutron scattering data permits structural analysis of the binding capability of LPS.

The consequence of LPS binding on gelsolin's actin severing capability is shown in FIG. 3. When added to purified human gelsolin, LPS inhibited 50% of the severing activity of the gelsolin and is a more potent inhibitor of either LPA (lysophosphatidic acid, which is a potent extracellular agonist) or PIP2. Lipid A, the LPS derivative lacking polysaccharide has a weaker but significant inhibitory effect, and nonspecific anionic lipids like PS have no effect. When added to whole human serum, LPS and PIP2 are also able to inhibit gelsolin activity, although larger amounts are needed as compared to inhibition of pure gelsolin in aqueous solution. LPA appears to be much less effective in serum than in pure solution, possibly because the greater lability of the lysolipid allows its more rapid partitioning into lipoprotein particles or Ca2+-mediated aggregates that are incapable of binding gelsolin.

Gelsolin competes with LBP (LPS-binding protein) for LPS. Using a solid phase binding assay, nanomolar concentrations of gelsolin were shown to inhibit binding of $^{125}$I-LBP to LPS coated wells by 69±6% (FIG. 3A). However, inhibition of LBP-LPS binding is not due to direct binding of LBP to gelsolin since $^{125}$I-LBP does not bind to gelsolin-coated surfaces (FIG. 3B). Since plasma contains higher levels of gelsolin (150-300 µg/ml), than that which is found in LBP (3-10 µg/ml) (Lind et al., 1988, supra; Mathison, 1992, supra), these data, showing comparable LPS affinity by gelsolin and by LBP, indicate that gelsolin may play a role in LPS-buffering or presentation.

One result of gelsolin-LPS binding is inhibition of the actin binding activity of gelsolin, as well as the actin depolymerizing activity of blood serum. Inhibition by LPS of actin depolymerizing activity in serum was shown to be due to its effect on gelsolin, because the actin-sequestering activity of Gc-globulin (or vitamin D-binding protein), which is the other component of the plasma actin scavenger system, was unaffected by LPS at concentrations at least up to 100 µM (data not shown). A 10-fold molar excess of LPS from *E. coli* (serotype 026:B6), *Salmonella enteritidis* (ATCC13076 strain) or *Pseudomonas aeruginosa* (serotype 10)(data not shown) effectively inhibited ~50% of gelsolin's actin filament severing capability. When added to purified human gelsolin, LPS inhibits the severing activity of gelsolin at a rate that increases with increasing concentration of LPS present (FIG. 4A). When added to whole human serum, LPS and PIP2 were also able to inhibit gelsolin activity, although larger amounts were needed compared to inhibition of pure gelsolin in aqueous solution (FIG. 4B).

Measurement of the effects on blood serum severing function showed that the inhibitory efficiency varies with the bacterial species from which LPS was released. For example, when several different LPS species were tested, the inhibitor effect was found to be *Klebsiella pneumoniae* (strain ATCC15380, Sigma)<*Salmonella enteritidis* (Strain ATCC 13076, Sigma)<*Escherichia coli* (data not shown). On a molar basis, LPS has proven to be a more potent inhibitor of gelsolin actin severing capability than either LPA or PIP2. Lipid A had a weaker, but still significant inhibitory effect, and nonspecific anionic lipids like PS had no effect (data not shown).

Therefore, it can be further concluded, by both chemical and physical evidence, that gelsolin binds LPS through its lipid-binding domain, and that the binding of polyphosphoinositides and LPA to gelsolin strongly inhibits gelsolin's actin filament severing function. Neutron scattering measurements suggest that LPS added to buffers in vitro forms micelles, and its interaction with gelsolin and other proteins may be different when it is in other complex forms. LPA appeared to lack its effect in serum, as compared to pure solution, possibly because the greater lability of the lysolipid allows its more rapid partitioning into lipoprotein particles or $Ca^{2+}$-mediated aggregates that are incapable of binding gelsolin.

Figures 5A, 5N:
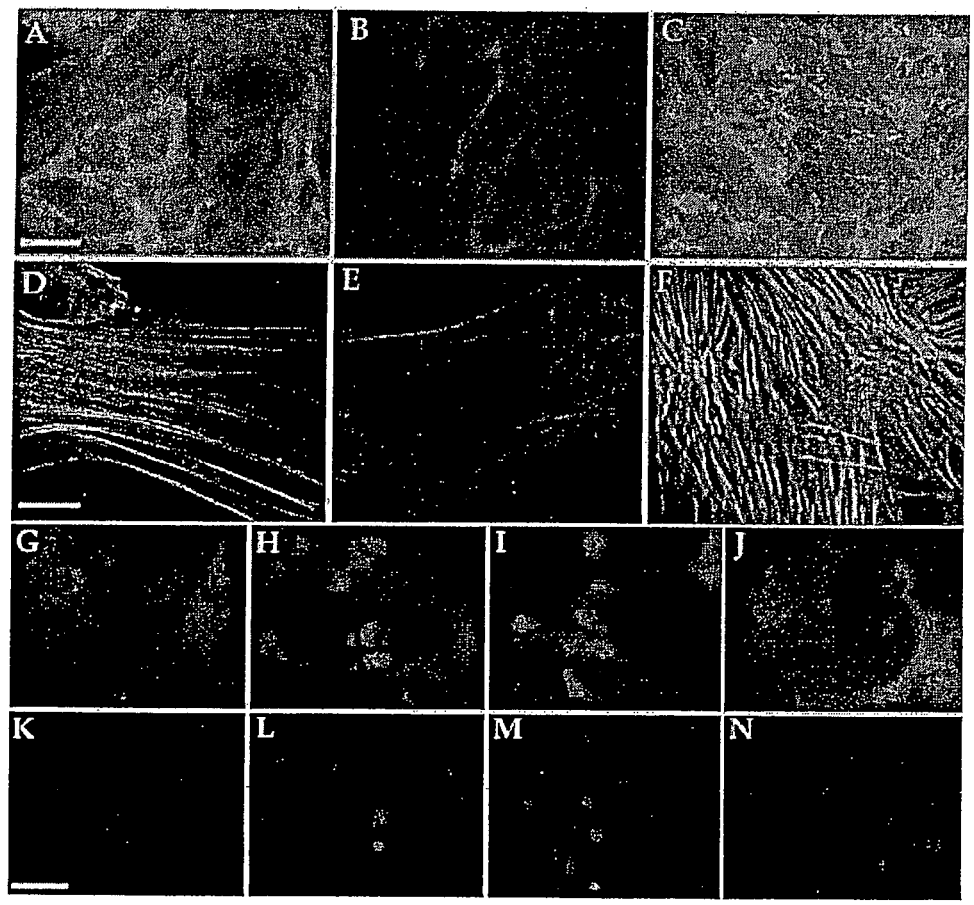
FIGS. 5A-5N photographically depict the LPS-induced disruption of cellular responses is inhibited by pre-incubating LPS with plasma gelsolin. Immunostaining for F-actin with phalloidin (FIGS. 5A-5F) was used to demonstrate the prevention by plasma gelsolin of LPS-induced actin cytoskeleton disassembly. Endothelial cells (FIGS. 5A-5C) and astrocytes (FIGS. 5D-5F) were treated with LPS (FIGS. 5B and 5E), or with a combination of LPS and gelsolin (FIGS. 5C and 5F). Control cells are also shown in FIGS. 5A and 5D. LPS induced NF-kB translocation to the nucleus was blocked by plasma gelsolin in FIGS. 5G-4N), as shown by immunostaining for NF-κB with an anti-NF-κB antibody (FIGS. 5G-5J) and cell nuclei with 4',6-diamidino-4-phenylindole dihydrochloride (FIGS. 5L-5M). In astrocytes, addition of TNF-α (FIGS. 5H and 5L), or 4 µM LPS (FIGS. 5I and 5M) caused NF-κB translocation to the nucleus, as compared with control cells (FIGS. 5G and 5K). Preincubation with gelsolin, however, blocked LPS-induced translocation (FIGS. 5J and 5N).

In a preferred embodiment of the invention, gelsolin prevents LPS-induced cellular effects in vitro. LPS effects on cellular functions, including cytoskeletal actin remodeling and collagen-induced platelet activation by pathways independent of toll-like receptors (TLR), are neutralized by gelsolin and by a peptide based on gelsolin residues 160-169 (SEQ ID No:1) which comprises part of gelsolin's phosphoinositide binding site. When added to either cultured human aortic endothelial cells (HAEC) or primary rat astrocytes, LPS at relatively high concentrations rapidly induced disassembly of the actin cytoskeleton (see disrupted and diffuse phalloidin staining in FIGS. 5B and 5E). By comparison, however, abundant actin bundles are seen in the controls (FIGS. 5A and 5D). However, when the LPS was first incubated with an excess of plasma gelsolin, the thus bound LPS had no discernable effect on the actin cytoskeletons of either the endothelial cells or the astrocytes.

TLR-dependent NF-kB translocation in fibroblasts appears not to be blocked by gelsolin (see Example 3), whereas LPS effects on cellular functions, including cytoskeletal actin remodeling by pathways independent of toll-like receptors (TLR) are neutralized by gelsolin and by a peptide based on gelsolin SEQ ID No:1. In untreated control astrocytes, NF-κB was located in the cytoplasm (FIG. 5G+K) and activation by LPS resulted in its translocation to the nucleoplasm (FIGS. 5I and 5M) similar to that induced by TNF-α (FIGS. 5H and 5L). However, the LPS-induced translocation of NF-κB (FIGS. 5I and 5M) was blocked by pre-incubation with gelsolin (FIGS. 5J and 4N). These results show a strong effect of LPS on plasma gelsolin function, and more importantly indicate that at least some effects of endotoxin in vivo are mediated or inhibited by plasma gelsolin.

Generalized coagulation dysfunction represents a common complication of LPS-induced septic shock syndrome. The effect of LPS on platelet function has reportedly depended on LPS concentration used to affect platelet function. It has be found that LPS at low concentration caused priming of platelets activation (Salat et al., *Leuk. Lymphoma* 33(1-2):25-32 (1999)), but LPS at 100-300 µg/ml inhibits platelets aggregation stimulated by collagen (Sheu et al., *Br. J. Haematol.* 103(1):29-38 (1998)). However, this LPS effect on collagen-induced platelet activation by pathways independent of toll-like receptors is neutralized by gelsolin. For example, when LPS was added alone, LPS strongly inhibited the aggregation and secretion of platelets induced by collagen (compare triangles to square symbols in FIG. 6). By comparison, the addition of gelsolin SEQ ID No:1 to LPS before it was added to the platelets, restored, in a peptide concentration-dependent manner, the normal collagen-induced activation and aggregation of the platelets. However, the gelsolin peptide (SEQ ID No:1) alone, as opposed to with LPS, had no effect on collagen-mediated platelet functions.

Figure 6:
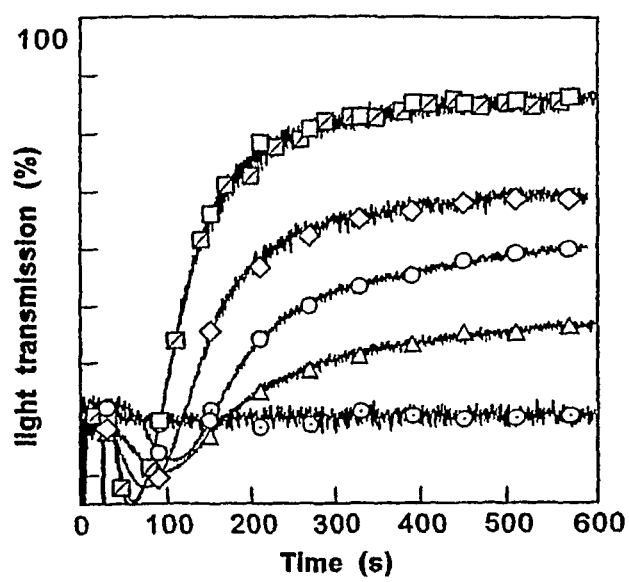
FIG. 6 graphically depicts the protective effect of gelsolin SEQ ID No:1 on LPS-mediated alteration of platelet function, i.e., platelet aggregation after stimulation by collagen, the effect of LPS inhibition, and reversal of the inhibition by gelsolin. Collagen±25 µM peptide (open squares); LPS±25 µM peptide+collagen (open diamonds); LPS+12 µM peptide+collagen (open circles); LPS+collagen (open triangles); 25 µM peptide (bottom line of open circles).

Therefore, FIG. 6 shows the protective effect of the gelsolin peptide SEQ ID No:1 (QRLFQVKGRR) (GLS 160-169) on LPS-mediated alteration of platelet function. These results show a strong effect of LPS on plasma gelsolin function and indicate that some of the pathogenic effects of endotoxin in vivo may be mediated, inhibited or even prevented by plasma gelsolin, or an active fragment thereof.

Since humans with sepsis have decreased plasma gelsolin concentrations (Suhler et al., 1997, supra), the effect of LPS administration on gelsolin levels can be studied in recognized mouse models. Intraperitoneal administration of *P. aeruginosa* LPS (serotype 10) caused a dose-dependent reduction in plasma gelsolin levels after 24 hours. The changes in gelsolin concentrations in response to LPS appear to be specific, because plasma albumin levels did not change. The modest reduction in plasma gelsolin level was consistent with the relatively low mortality (35% by 7 days after treatment) of mice receiving 40 mg/kg of *P. aeruginosa* LPS. In contrast, mice challenged with LPS from *E. coli* (serotype 055:B5) at 25 mg/kg decreased their plasma gelsolin values by 50% within 24 hours after challenge, and had a 100% mortality rate by 7 days (data not shown).

In a preferred embodiment of the invention, however, the mice are administered human recombinant plasma gelsolin (GSN) subcutaneously, immediately after challenge with *E. coli* LPS, and daily thereafter for three additional doses. The mortality rate is then compared with those treated with saline solution alone, or with bovine serum albumin (BSA). The gelsolin amounts administered by this route restore plasma levels in LPS-treated animals to 200 µg/ml, which is slightly greater than the baseline concentrations (data not shown). However, mice treated with plasma gelsolin have markedly improved survival compared to saline or BSA controls (data not shown). At Day 7, the surviving mice (all in the GSN group) all appear to have complete recovery and exhibit no signs of distress.

Gelsolin Interaction with Lipoteichoic Acid (LTA)

Bacterial sepsis can also result from gram-positive bacterial infections that do not produce LPS, but rather, that have LTA as their major outer wall constituent. As shown in FIG.

Figure 7A:
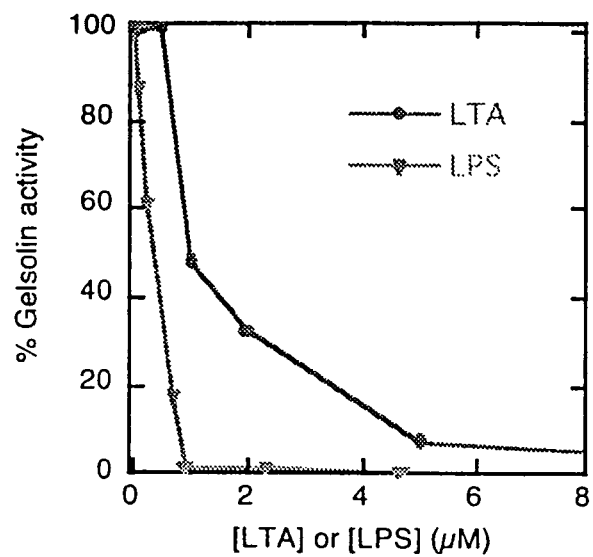
FIG. 7A-7B graphically depict interactions of LTA with gelsolin.
Figure 7B:
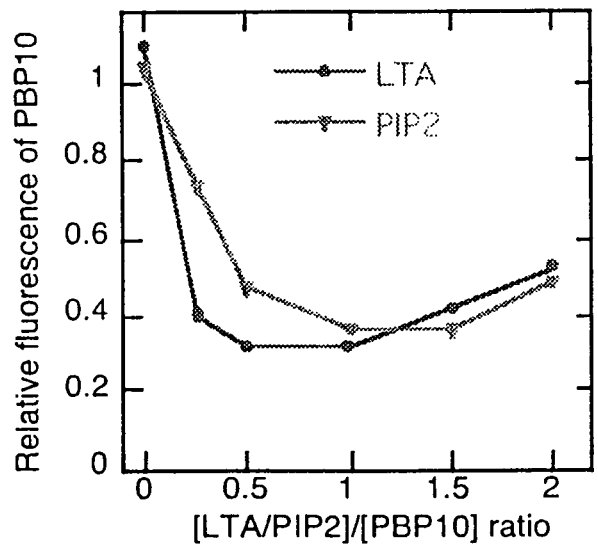

7A-7C, LTA binds to gelsolin approximately as strongly as do LPS and PIP2. LTA is a potent inhibitor of gelsolin's actin filament severing activity (FIG. 7A) and binds to the PIP2-binding site within the PBP10 peptide (FIG. 7B), suggesting that LTA, LPS, and PIP2 all bind to at least one common site within gelsolin.

As seen in FIG. 8, gelsolin prevents LTA activation of endothelial cells as measured by neutral adhesion, meaning that it prevents LTA-mediated HAEC activation. The same active region is involved in gelsolin for both LPS, and for LTA. Gelsolin may be used in septic conditions after infection with gram-negative and gram-positive bacteria, regardless of the bacteria causing the infection. Because the physical chemistry of LPS and LTA are similar, their inflammatory effects share certain common features. Recent in vitro studies show that they bind at least some of the same plasma protein ligands, and they stimulate the same membrane receptors (e.g., TLR-2). As a result, based upon the protective effect of gelsolin on LPS in vivo demonstrated in the examples that follow, a similar protective effect is encompassed in an alternative embodiment of the present invention by animal studies of gelsolin and LTA.

Gelsolin Interaction with Acidic Lysolypids

The acidic lysolipids sphingosine phosphate (S1P) and sphingosyl phosphocholine (SPC) also inhibit gelsolin, indicating their interaction. Although previous studies had reported that S1P does not bind gelsolin or other related proteins like fragment (Meerschaert et al., supra, 1998), the potent activity of LPS motivated reinvestigation of S1P for the purposes of the present invention because S1P shares with PPIs, LPA and LPS the rare presence of a phosphomonoester at its hydrophilic domain. S1P is also a potent bioactive signal that rises during bacterial sepsis and other inflammatory disorders and that might relate to the protective effect of gelsolin infusion after LPS injection.

As shown in FIG. 9, S1P inhibits gelsolin as least as strongly as LPA does when added at concentrations below 1 µM, but shows an abrupt drop-off of activity at higher concentrations. SPC, another mediator of cell function has similar effects as S1P, but other bioactive lipids, such as platelet activating factor (PAF) do not inhibit gelsolin.

The relatively low activities of S1P and SPC at high concentrations are very likely due to the limited solubility of S1P and SPC in aqueous buffer near neutrality. The structural state of S1P and it optimal conditions for its solubility have not yet been determined (Li et al., *Chem. Phys. Lipids* 130:197-2012 (2004)). It may be relevant that the levels of S1P in normal blood plasma obtained from healthy donors are between 0.5 and 1 µM, and that arise in S1P levels is negatively related to the efficiency of platelet aggregation in such plasma samples (Igarashi et al., *Am. J. Hematol.* 57:261-262 (1998); Nugent et al., *Platelets* 11:226-232 (2000)).

The tight and selective binding of gelsolin to LPS and LTA may have several implications for the function of plasma gelsolin and may suggest methods to counteract the toxic effects of LPS and LTA. The wide distribution of a extracellular gelsolin protein in eukaryotic species, including humans, and its binding to a variety of endotoxins suggests that it is a component of the innate immune system (Beutler et al., *Crit. Care Med.* 29 (supplement) S2-S7 (2001)). The findings presented in this invention support the concept of a strong clinical correlation between lowered gelsolin levels due to primary injury and susceptibility to secondary complications may result from a loss of buffering of inflammatory lipid mediators. The lack of reported human antibodies directed against gelsolin indicates that this normal plasma constituent has a high degree of structural conservation between individuals. Therefore, it is a preferred embodiment of the present invention to provide methods of using gelsolin as a potential treatment for the sepsis syndrome.

Transgenic constructs may be generated comprising an isolated nucleic acid comprising the nucleic or amino acid sequence of gelsolin or an active fragment thereof. Suitable vectors include, but are not limited to, plasmids containing a sense or antisense strand placed under the control of the strong constitutive promoter or under the control of an inducible promoter. Methods for the generation of such constructs are well known in the art once the sequence of the desired gene is known. Suitable vector and gene combinations will be readily apparent to those of skill in the art.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds, which facilitate transfer of nucleic acid into cells, such as, for example, polylysine compounds, liposomes, and the like. "Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

The nucleic acid encoding the gelsolin peptide can be duplicated using a host-vector system and traditional cloning techniques with appropriate replication vectors. A "host-vector system" refers to host cells, which have been transfected with appropriate vectors using recombinant DNA techniques. The vectors and methods disclosed herein are suitable for use in host cells over a wide range of eukaryotic organisms. This invention also encompasses cells transformed with the replication and expression vectors, using methods known in the art. Indeed, a gene encoding the modulating nucleic acid, such as the nucleic acid sequence encoding gelsolin can be duplicated in many replication vectors, and isolated using methods described, e.g., in Sambrook et al., 1989.

The selected gene, made and isolated using the above methods, can be directly inserted into an expression vector, such pcDNA3 (Invitrogen) and inserted into a suitable animal or mammalian cell. In the practice of one embodiment of this invention, the gene or gene fragment, such as the purified nucleic acid molecule encoding, e.g., gelsolin, is introduced into the cell and expressed. A variety of different gene transfer approaches are available to deliver the gene or gene fragment encoding the modulating nucleic acid into a target cell, cells or tissues.

As used herein, "recombinant" is intended to mean that a particular DNA sequence is the product of various combination of cloning, restriction, and ligation steps resulting in a construct having a synthetic sequence that is indistinguishable from homologous sequences found in natural systems. Recombinant sequences can be assembled from cloned fragments and short oligonucleotides linkers, or from a series of oligonucleotides. As noted above, one means to introduce the nucleic acid into the cell of interest is by the use of a recombinant expression vector. "Recombinant expression vector" is intended to include vectors, capable of expressing DNA sequences contained therein, where such sequences are operatively linked to other sequences capable of effecting their expression. It is implied, although not always explicitly stated, that these expression vectors must be replicable in the host organisms, either as episomes or as an integral part of the chromosomal DNA. Suitable expression vectors include viral vectors, e.g., adenoviruses, adeno-associated viruses, retroviruses, cosmids and others, typically in an attenuated or non-replicative form. Adenoviral vectors are a particularly effective means for introducing genes into tissues in vivo because of their high level of expression and efficient transformation of cells, both in vitro and in vivo.

Accordingly, when reference is made herein to "administering" gelsolin or a functionally equivalent peptide fragment thereof to a patient, it is intended that such methods include not only delivery of an exogenous composition to the patient, but also methods for increasing expression levels of the gelsolin within the patient. Expression levels of the gene or nucleotide sequence inside a target cell are capable of providing gene expression for a duration and in an amount such that the nucleotide product therein is capable of providing a therapeutically effective amount of gene product or in such an amount as to provide a functional biological effect on the target cell. By "gene delivery" is meant transportation of a composition or formulation into contact with a target cell so that the composition or formulation is capable of being taken up by means of a cytotic process into the interior or cytoplasmic side of the outermost cell membrane of the target cell, where it will subsequently be transported into the nucleus of the cell in such functional condition that it is capable of achieving gene expression.

By "gene expression" is meant the process, after delivery into a target cell, by which a nucleotide sequence undergoes successful transcription and translation such that detectable levels of the delivered nucleotide sequence are expressed in an amount and over a time period that a functional biological effect is achieved. "Gene therapy" encompasses the terms gene delivery and gene expression. Moreover, treatment by any gene therapy approach may be combined with other, more traditional therapies.

By "patient" or "subject" is meant any vertebrate or animal, preferably a mammal, most preferably a human, that is affected by or susceptible to endotoxin-induced sepsis or inflammation-induced pulmonary microvascular dysfunction. Thus, included within the present invention are animal, bird, reptile or veterinary patients or subjects, the intended meaning of which is self-evident. The methods of the present invention are useful in such a patient for the treatment or prevention of the following, without limitation: septic shock, pathogenesis relating to a severe burn, myocardial infarction, acute hepatic failure, myonecrosis, acute lung injury, and adult respiratory distress—multiple organ dysfunction syndrome (ARDS/MODS).

In another embodiment of the present invention, the gelsolin or gelsolin active fragment (SEQ ID No:1) is designed by mimetics for synthetic production. The designing of mimetics to a pharmaceutically active compound is a known approach to the development of pharmaceuticals based on a "lead" compound. This might be desirable where the active compound is difficult or expensive to synthesize or where it is unsuitable for a particular method of administration. Mimetic design, synthesis and testing is generally used to avoid randomly screening large number of molecules for a target property, see, e.g., U.S. Pat. Nos. 5,071,773; 5,750,353; 5,925,529; 5,744,303; 5,569,588; and 5,407,821.

The invention further provides an assay for determining agents, which bind to, neutralize or inhibit LPS, LTA, or other factors in a sequence of events leading to the onset of endotoxemic sepsis or inflammation-induced pulmonary microvascular dysfunction, thereby reducing, modulating or preventing such pathologies. Such an assay comprises administering an agent under test to the cells or model animals, such as those described herein at low cell density, and monitoring the onset or severity of sepsis or microvascular dysfunction. A further assay according to the invention comprises administering the agent under test to photoreceptor cells at high cell density, and monitoring the onset or severity of sepsis or microvascular dysfunction. Agents may thus be selected which effectively reduce, inhibit, neutralize or prevent sepsis, microvascular dysfunction, ARDS or the like. The agents thus selected, are also intended to be a part of the present invention.

In yet another embodiment, sensitivity of gelsolin levels in vivo are used as a biomarker for measuring disease severity in sepsis or inflammation, or for determining levels of bacterial endotoxins.

In accordance with the present invention, the gelsolin, or fragment thereof, intended to bind to, neutralize or inhibit LPS, LTA, F-actin-binding proteins or other factors in a sequence of events leading the onset of endotoxemic sepsis, thereby reducing, modulating or preventing such sepsis or inflammatory response, as described above, when used in therapy, for example in the treatment of an endotoxemic patient or one infected with a gram-positive or gram negative bacteria, can be administered to such a patient either alone or as part of a pharmaceutically acceptable composition, and optionally with a preservative, diluent, and the like. They may further be administered in the form of a composition in combination with a pharmaceutically acceptable carrier or excipient, and which may further comprise pharmaceutically acceptable salts. Examples of such carriers include both liquid and solid carriers, such as water or saline, various buffer solutions, cyclodextrins and other protective carriers or complexes, glycerol and prodrug formulations. Combinations may include other pharmaceutical agents.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Various methods of "administration" of the therapeutic or preventative agent can be used, following known formulations and procedures. Although parental administration is described herein and is generally preferred, systemic or targeted administration may also be employed under suitable circumstances. Compounds or compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, saline, buffered saline, dextrose, ethanol, glycerol, polyols, and the like, and suitable mixtures thereof. Proper fluidity can be maintained, for example, by the use of a coating, such as lecithin, by the maintenance of the required particle size in the case of dispersions and by the use of surfactants. These compositions may also contain adjuvants, such as preserving, wetting, emulsifying, and dispensing agents. Sterility can be ensured by the addition of various antibacterial and antifungal agents. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Amounts and regimens for the administration of gelsolin or related actin-binding compounds can be determined readily by those with ordinary skill in the clinical art of treating actin-related disorders, tissue injury or inflammation. Generally, the dosage of gelsolin or related actin-binding compound treatment will vary depending upon considerations, such as: age; health; conditions being treated; kind of concurrent treatment, if any, frequency of treatment and the nature of the effect desired; extent of tissue damage; gender; duration of the symptoms; and, counter-indications, if any, and other variables to be adjusted by the individual physician. Dosage can be administered in one or more applications to obtain the desired results (see, e.g., dosages proposed for human therapy by Rothenbach et al., 2004, supra).

The dosage can be calculated in the following manner. If the normal blood gelsolin concentration is 2.4 µM (2.4 µmol/l), and the normal blood DBP concentration is 5 µM (5 µmol/l). Thus, the total blood actin-binding capacity (ABC) is approximately 7.5 µmol/l. The blood volume is 6% of the body weight, hence a 70 kg person has about 4.2 liters of blood and as a result, 4.21×7.5 µmol/l=31.5 µmols ABC. Since gelsolin is distributed throughout the extracellular space (which is ~10% of body weight), the body contains 7.5×7=52.5 µmols gelsolin ABC.

It may be desired to administer between 32 and 53 µmols of gelsolin (or 0.46 µmol/kg body weight) to cover total complexing or depletion of endogenous gelsolin or other actin binding compounds. Plasma concentration of endogenous gelsolin in normal, uninjured humans is 211 µg/ml, and in rabbits, 368 µg/ml (Lind et al., 1986, supra). Since 0.425 mg of actin is equal to 1 µmol, and since there is 4.86 mg actin per gram of skeletal muscle, each gram of muscle contains about 11.3 µmol actin. Thus, 4.6 g of muscle destruction could neutralize total body gelsolin or other actin binding compounds. However, because the toxic effects of actin are presumably local (e.g., inhibition of clot lysis), sequestered or kinetically determined (e.g., actin permeates an organ faster than binding proteins neutralize it), it is likely that a theoretically minimum dose will have to be adjusted upward in order to achieve kinetically favorable therapeutic effects. The kinetic effect can be important since there is apparently slow equilibration between extravascular and blood compartments acutely (Smith et al., 1988, supra). Conversely, a therapeutically effective state, capable of breaking up local deposits of actin, may be achievable only by a transient pulse of a high concentration of gelsolin or actin-binding molecules.

Instead of administering the gelsolin or gelsolin peptides or other binding compounds directly, they can also be produced in the target cells by expression from an encoding gene introduced into the cells, e.g., in a viral vector. The vector could be targeted to the specific cells to be treated, or it could contain regulatory elements, which are switched on more or less selectively by the target cells. Increased expression is referred to as up-regulation.

By "therapeutically effective" as used herein, is meant that amount of composition that is of sufficient quality and quantity to neutralize, ameliorate, modulate, or reduce the cause of or effect of endotoxin caused sepsis or inflammation. Because the gelsolin lipid-binding activity is $Ca^{2+}$-mediated, it is assumed when the term "therapeutically effective," with regard to administration of gelsolin or the functionally equivalent peptide fragment thereof, that $Ca^{2+}$ or other necessary divalent ion is present at the levels necessary to activate the gelsolin molecule. By "ameliorate," "modulate," or "reduce" is meant a lessening or reduction or prophylactic prevention of the detrimental effect of the disorder in the patient receiving the therapy, thereby resulting in "protecting" the patient. A "sufficient amount" or "effective amount" or "therapeutically effective amount" of an administered composition is that volume or concentration which causes or produces a measurable change from the pre-administration state in the cell or patient. The subject of the invention is preferably a human patient, however, it can be envisioned that any animal with endotoxemia or sepsis can be treated in a method of the present invention. As used herein, the terms "treating" and "treatment" are intended to include the terms "preventing" and "prevention." One embodiment of the present invention includes the administration of gelsolin or fragment thereof in an amount to treat or prevent sepsis and inactivate bacterial endotoxin.

By "inhibition" or "blocking" refer to a statistically significant reduction in inflammation or in toxins that cause inflammation (sepsis) associated with LPS or LTA, as compared with a selected standard of activity or for cells or tissues grown without gelsolin. Preventing refers to effectively 100% levels of prophylactic inhibition. Preferably, the increased levels of gelsolin (meaning a higher concentration than was present before additional gelsolin was added or before gelsolin expression was up-regulated in the patient) reduces sepsis or risk of sepsis by at least 20%, more preferably by at least 50%, even more preferably by 80% or greater, and also preferably, in a dose-dependent manner.

The invention is further defined by reference to the following specific, but nonlimiting, examples that describe in detail the preparation of exemplary injectable compositions and methods using them for tissue engineering. Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory, N.Y. (1982) and Sambrook et al., Molecular Cloning: A Laboratory Manual, Cold Spring Harbor Laboratory, N.Y. (1989) and the various references cited therein. It will be apparent to those skilled in the art that many modifications, both to materials and methods, may be practiced without departing from the purpose or narrowing the scope of this invention.

EXAMPLES

Example 1

Gelsolin Binding and Severing Capabilities

Binding Activity

To provide chemical and functional evidence that gelsolin binds LPS through its lipid-binding domain, a solid phase assay was conducted in which radiolabeled LPS was added to wells coated with different amounts of rhodamine-B-labeled-SEQ ID No:1 (rhodamine-B-QRLFQVKGRR, derived from the PIP2-binding site of gelsolin and termed "PBP10"), or to a truncated peptide (rhodamine-B-QRL), in the absence or presence of unlabeled LPS, respectively.

SEQ ID No:1 (QRLFQVKGRR) gelsolin residues 160-169, and QRL peptides, were prepared by solid phase peptide synthesis on p-benzyloxybenzyl alcohol/polystyrene resin using alpha-Fmoc protection chemistry and carbodiimide/N-hydroxybenzotriazole coupling as taught by Cunningham et al., *J. Biol Chem* 276:43390-9 (2001)). The side chains were protected as follows: Arg (Pmc), Gln (Trt), Lys (Boc). To couple fluorophores onto these peptides, ester derivatives of each fluorophore were created and linked directly to the N-terminus of the peptides on the solid phase support. After coupling, the peptides were cleaved from the solid support with trifluoroacetic acid and phenol (95:5, v/w). All peptides were purified by reverse phase HPLC on a silica C-18 column using a 20-60% acetonitrile gradient in 0.1% trifluoroacetic acid and dried (Cunningham et al., 2001, supra).

To determine the interaction of LPS with gelsolin and fluorescence peptides derived from gelsolin PIP2 binding site, the fluorescence of rhodamine B-peptide SEQ ID No:1 or emissions spectra of pyrene-peptide SEQ ID No:1 (QR-LFQVKGRR) ($\lambda$em 590 nm, $\lambda$ex 560 nm, or $\lambda$em 365-550 nm, $\lambda$ex 343 nm, respectively) was measured fifteen minutes after addition of various concentrations of LPS (*Escherichia coli* serotype 026:B6, Sigma), PIP2, LPA or PS added to 2 μM solutions of the peptides in buffer A (10 mM TRIS, 10 mM MES (2-morpholinoethane-sulfonic acid), pH 7.0. Since the surface concentration of the peptides bound to the lipids will become much higher than their bulk concentration, peptide binding was demonstrated by changes of either rhodamine-B fluorescence or formation of pyrene-excimers, with a shift of fluorescence emission from the monomer wavelength at 378 nm to the excimer emission at 473 nm. Therefore, to determine changes of gelsolin OD at 280 nm, different amounts of LPS, LPA and PS were added to recombinant human gelsolin (rhGLS) solutions and OD emission spectra were recorded using spectrophotometer Genesys 6 (Thermo-Spectronic, USA).

Solid Phase Assay

Tritium-labeling of LPS was done by a modification of the procedure of Watson and Riblet (Watson et al., *J. Immunol* 114:1462-8 (1975)). A sample (2 mg) of LPS from *Salmonella minnesota* Re595 (Sigma Chemical Co., St. Louis, Mo.) was oxidized (150 minutes, 20° C.) with sodium periodate ($3\times10^{-2}$ M). After destruction of the oxidant with 1.0 M ethylene glycol, aldehyde groups were reduced (18 hours at 4° C.) with an ice-cold solution of NaB [$^3$H]$_4$ (0.46 GBq, 481 GBq/mmole, wherein GBq refers to a unit of radioactivity) (Amersham-Pharmacia Biotech, Buckinghamshire, England) in 200 μl of ice-cold borate buffer (0.05 M, pH 9.5). Excess sodium borohydride was destroyed with 5 μl of acetic acid. After two washings (centrifugation at 100,000×g for 15 minutes) in 400 μl of an ice-cold water-ethanol mixture (1:1 by vol.), the radiolabeled [$^3$H]-LPS ($9\times10^5$ cpm/μg; $2\times10^3$ cpm/pmole) was stored at −20° C. until used.

To measure [$^3$H] labeled-LPS-binding, polystyrene ELISA-type microplates (96 wells) were coated with PBP10 or rhodamine-B-QRL (RhB-QRL) by incubation for 18 hours at 4° C. with a solution (100 μl, 500 pmole/well) in saline. After three washings with 100 μl saline, the wells were then incubated at room temperature with [$^3$H]-LPS (360,000 c.p.m.), in the presence or absence of unlabeled LPS (20 μg/well), in a binding medium (100 μl) containing bovine serum albumin (50 μg) in saline. After 3 hours of incubation, the plates were washed three times with 100 μl saline washes, and the remaining bound radioactivity was measured.

The results are shown in FIG. 1A of the solid phase assay, wherein radiolabeled LPS was added to wells coated with different amounts of PBP10 peptides±cold LPS. The results in the absence of unlabeled LPS is shown as open circles, while the presence of unlabeled LPS is shown as open triangles. As shown, LPS saturably bound PBP10, and resulted in substantial inhibition of labeled LPS binding in the presence of excess LPS. By comparison, the truncated peptide (rhodamine-B-QRL) did not bind LPS.

FIG. 1B, showing the optical density (OD) of gelsolin in solutions containing varying amounts of LPS or LPA, demonstrates the interaction of LPS or PIP2 with intact gelsolin. Both LPS and PIP2 induced identical concentration-dependent fluorescence quenching of PBP10, indicating insertion of the peptide-bound rhodamine into a more hydrophobic environment. LPA also diminished the absorbance of gelsolin, but PS had no effect. LPS and PIP2 also caused congruent changes in the fluorescent spectrum of pyrene-QR-LFQVKGRR (Bucki et al., *Biochemistry* 40:15752-61 (2001)) in which binding to these lipids—but not to PS—induced clustering of the peptide with resulting excimer fluorescence of the pyrene group, manifest as a large increase in fluorescence emission at 480 nm (data not shown).

The fluorescence of rhodamine-B-SEQ ID No:1 (QR-LFQVKGRR) was also changed by LPS as shown in FIG. 1C. There was also no fluorescence change after adding LPS to a control peptide with the sequence rhodamine B-QRL (RhB-QRL, data not shown).

Interaction of LPS and gelsolin was examined using rhodamine B- and pyrene-labeled SEQ ID No:1 (QR-LFQVKGRR). The effect of LPS on gelsolin was determined in terms of the rhodamine-B fluorescent changes of PBP10 peptide in the presence of different lipids (FIG. 1C); and the fluorescence emission spectra of pyrene-labeled SEQ ID No:1 (2 μM) in the presence of LPS from *Escherichia coli* (1.2 μM), PIP2 (0.82 μM) and LPA (0.82 μM) (FIG. 1D) The results using the pyrene-derivatized gelsolin peptide confirmed the LPS induced clustering of the peptide with resulting excimer fluorescence of the pyrene group, which was evident as a large increase in fluorescence emission at 480 nm. LPS, LPA, and PIP2 had similar abilities to induce excimer formation, whereas PS had no effect (data not shown).

Alternative assays could also be used to confirm the binding characteristics of LPS to gelsolin. One test uses radiolabeled LPS and assays for gelsolin by affinity chromatography using immobilized anti-gelsolin antibody (a similar assay was used to detect binding of $^{32}$PIP2 to gelsolin (Janmey et al., *Nature* 325:362-364 (1987). Glass tubes containing phosphatidylcholine (PC) (0.3 mg) alone or mixed with the material to be tested (gelsolin, gelsolin half-mutant lacking PIP2 binding site, PBP10 peptide, etc) is evaporated to dryness. After sonication with a solution of BSA (60 μl, 1 mg/ml in 0.15 M NaCl), the vesicles are incubated (2 hours, 20° C.) under gentle rotation, with [$^3$H]-LPS. Then the density is adjusted to 1.185 g/ml by addition of 350 μl of a solution of 1.1% NaCl and 46% NaBr. A discontinuous gradient will be prepared by sequential addition of 23% NaCl (700 μl) and the radioactive suspension (700 μl), 20.5% NaCl (700 μl), 16.5% NaCl (700 μl), and 8% NaCl (200 μl). After centrifugation (65,000 g, 90 minutes), the radioactivity of collected fractions is measured by liquid scintillation. Vesicles with bound radiolabeled LPS are recovered at the top (1 ml) of the density gradient, whereas unbound [$^3$H]-LPS was found at the bottom. The LPS-binding index of a compound is defined as the radioactivity recovered at the top (1 ml) of the density gradient, expressed as a percentage of the total radioactivity recovered.

Measurement of Complexes by Neutron Scattering

The molecular structure of LPS and its complexes with proteins can be measured at nm resolution by X-ray and neutron scattering, as well as by electron and atomic force microscopy. FIG. 2 shows preliminary neutron scattering measurements of the effects of gelsolin peptide SEQ ID No:1 on LPS structure.

The linearity of the plot of ln(QI(Q)) vs. Q2 suggests that LPS forms a cylindrical structure under the conditions used, consistent with an earlier neutron scattering study (Hayter et al., *J. Biol. Chem.* 262:5100-5105 (1987)). The small, but significant increase in calculated diameter of LPS when the gelsolin peptide is added, suggests an alteration of the diameter. At present these data only serve to confirm that sufficiently good scattering data can be gathered for structural analysis. At present, the calculated diameter (36 nm) is greater than that which has been previously reported for pure LPS micelles, and the difference in size may reflect another structural feature. In additional experiments with more variations in gelsolin/LPS or peptide, LPS ratios will reveal if there are significant changes in LPS particle structure when these peptides bind LPS.

Further neutron scattering studies can be done at Argonne National Laboratories where the present data were taken. Each such measurement takes about 4 to 6 hours of beam time, so specimens are limited to selected conditions in which DLS or electron microscopy suggests novel structures formed by LPS and gelsolin, and where the biological activity of LPS is inhibited. Transmission electron microscopy of these complexes will also be done. If lamellar ribbon-like structures, similar to those formed by PEP2 and gelsolin, geometrically the headgroups may be occluded in the interior of the ribbon, and if similar structures are seen when adding gelsolin to LPS, the removal of the charged groups of LPS from the surface of the structure may relate to a loss of its cellular effects.

Example 2

Gelsolin Competes with LPS-binding Protein (LBP) for LPS

To determinate whether gelsolin can effect an action similar to LBP-mediated incorporation of LPS into blood lipoprotein an experiment is utilized, in which repartition of Bodipy- or $^3$H-labeled-LPS to reconstituted HDL (R-HDL) or plasma lipoproteins is measured. R-HDL is prepared by mixing apo A-1, egg PC, cholesterol and cholate at molar ratio 1:80:4:80 followed cholate dialysis as previously described by Yu et al., 1997, supra. The fluorescence of Bodipy-LPS in micelles is quenched, but quenching is relieved and fluorescence increases upon movement of Bodipy-LPS monomers out of aggregates. An increase in fluorescence is observed when both gelsolin and R-HDL are mixed with Bodipy-LPS provides evidence for gelsolin-depended transfer of LPS to R-HDL, similar to that seen with LBP. Pure LPS and various amounts of gelsolin are added to observe if gelsolin alone changes the Bodipy-LPS fluorescence, since any such change will have to be subtracted from the initial fluorescence after adding lipoproteins. The rate and extent of fluorescence change after lipoprotein addition offers a means for monitoring exchange of LPS into the lipoprotein particles. For purified systems, lipoprotein size is also measured by dynamic light scattering. Since DLS data are heavily weighted by the largest particles, the average hydrodynamic diameter will be nearly equal to that of lipoproteins alone, and any change indicates that the particles are fragmented or fused by gelsolin/LPS.

Since fluorescence measurements are strongly perturbed in plasma or serum, partitioning is examined of $^3$H-labeled-LPS to blood plasma lipoprotein fractions in gelsolin-depleted samples using anti-gelsolin coated sepharose 2B beads as done previously by Janmey et al., 1987, supra, or in plasma of gelsolin-null mice after adding back various concentrations of gelsolin. Because the interactions of two other known plasma proteins: a soluble form of CD14 receptor (sCD14) and plasma LBP (their plasma concentration is 2-6 µg/ml and 3-10 µg/ml respectively), may interfere with this assay, these proteins are also be removed by sepharose 2B beads coated with their respective antibodies.

To determine competition between gelsolin and LPS-binding proteins (LPB), a high affinity carrier for LPS, the LPS-coated wells (1 nmole/per well of LPS Re-595 from *Salmonella minnesota*) were saturated by incubation (2 hours, 20° C.) with gelsolin 2 mg/ml in RPMI), washed and preincubated with different amount of recombinant human gelsolin (0-2 ng/well) in gelsolin (0.5 mg/ml) containing RPMI. RPMI medium refers to Roswell Park Memorial Institute medium, typically used to culture human lymphoid cells. Then, 10 µl of $^{125}$I-LPB ($6\times10^4$ cpm) were added, and the plates were incubated for 90 minutes at 37° C., then washed six times with RPMI. After that, the bound radioactivity was measured. Similarly, gelsolin-coated wells were used to demonstrate whether rhGLS directly interacts with $^{125}$I-LPB.

It was shown that nanomolar concentrations of gelsolin inhibited the binding of $^{125}$I-LBP (LPS-binding protein) to LPS coated wells by 69±6% (FIG. 3A). Moreover the inhibition of LBP-LPS binding was not due to the direct binding of LBP to gelsolin, since $^{125}$I-LBP did not bind to gelsolin-coated surfaces (FIG. 3B). Because plasma contains higher levels of gelsolin (150-300 µg/ml), than the gelsolin in LBP (3-10 µg/ml) these data, showing comparable affinity of gelsolin and LBP for LPS, demonstrate that gelsolin plays a role in LPS-buffering or presentation.

Example 3

Gelsolin's Actin Filament Severing Activity and Effect of LPS

To determine gelsolin's severing activity, rates of fluorescence decrease were evaluated during depolymerization. Monomeric G-actin was prepared from an acetone powder of rabbit skeletal muscle according to previously published methods (Spudich et al., *J. Biol. Chem* 216:4866-4871 (1975)). The non-polymerizing solution contained 2 mM TRIS, 0.2 mM $CaCl_2$, 0.5 mM ATP (adenosine triphosphate), 0.2 mM DTT (dithiothreitol) pH 7.4. Actin was polymerized by adding 150 mM KCl and 2 mM $MgCl_2$ to the G-actin solutions and incubating for 1 hour at room temperature.

For F-actin severing assays, in general, a small volume (typically 5 µl) of the gelsolin composition is added to a similar volume of pyrene-labeled F-actin at a concentration adjusted to provide an actin:gelsolin ratio of approximately 10:1 (typically 1 µM gelsolin and 10 µM actin). This mixture is the diluted to 0.5 µM in a larger volume of F-actin buffer, and the filament severing efficiency is calculated from the initial slope of the fluorescence change. This reflects the rate of depolymerization that, in turn, is proportional to the number of cuts made by gelsolin. The LPS/gelsolin reaction can be done under any ionic condition, and the addition to F-actin requires the presence of ≥µM $Ca^{2+}$ to activate the gelsolin. However, since the severing reaction requires only a few seconds, and the effects of $Ca^{2+}$ on lipid aggregate size is slower and, at least for gelsolin/PIP2 does not reverse any complexes formed under other ionic conditions, it is possible, to a large extent, to alter the ionic conditions at which gelsolin binds LPS. The actin nucleation reaction is similar except that in the latter case, the gelsolin/LPS mixture is added to a more dilute solution of G-actin (typically, 1 or 2 µM) in low ionic strength buffer followed immediately by addition of 150 mM KCl and 2 mM $MgCl_2$ to initiate polymerization.

Any difference observed for binding of LPS to gelsolin or PBP10 by fluorescence assays in the present invention are also evaluated by the filament severing and nucleation tests.

As shown, recombinant human gelsolin (rhGLS) (FIG. 4A) and blood serum (FIG. 4B) severing activity was measured in 0.4 μM pyrene-labeled F-actin samples (polymerized with 50% pyrene-labeled G-actin), after adding gelsolin (16 nM)/serum (2.5 μl), or their combination with one of the following: LPS (from different species), PIP2 (phosphatidylinositol-4,5-bisphosphate), LPA (lysophosphatidic acid), lipid A (the LPS derivative lacking polysaccharide) or PS (phosphatidylserine). The fluorescence intensity of F-pyrene actin was then monitored for 10 minutes, and the severing activity was calculated based on decreasing fluorescence. Severing activity was determined from a decrease in rate of fluorescence during depolymerization, and the depolymerization rate was calculated from the slope of the early decrease in fluorescence.

When added to purified human gelsolin, 0.02 μM LPS (100 ng/ml) inhibited 50% of the severing activity of 0.016 μM gelsolin, and severing capability was 90% inhibited by a 10-fold increase to 0.1 μM LPS (FIG. 4A). On a molar basis, LPS was found to be a more potent inhibitor than either LPA or PIP2. A 10-fold molar excess of LPS from *E. coli* (serotype 026:B6) (FIG. 4A), *Salmonella enteritidis* (ATCC13076 strain) or *Pseudomonas aeruginosa* (serotype 10) (data not shown) effectively inhibited the ability of gelsolin to sever actin filaments. Lipid A had a weaker but still significant inhibitory effect, and nonspecific anionic lipids like PS had no effect (data not shown). When added to whole human serum (FIG. 4B), LPS and PIP2 were also able to inhibit gelsolin activity, although larger amounts were needed compared to inhibition of pure gelsolin in aqueous solution.

Example 4

Gelsolin Prevents LPS-induced Cellular Responses to LPS in Vitro

In light of the findings in the previous Examples, and using the materials prepared in above, the effect of the gelsolin binding by LPS was studied to determine the effect on cellular responses in vitro. Cell cultures of human aortic endothelial cells (HAEC) and rat primary astrocytes were used to evaluate the effect of LPS on actin. Both of these cell types have mCD14 (membrane bound C14) and TLR LPS receptors (Faure, et al., *J. Biol. Chem.* 275:11058-11063 (2000); Bsibsi, et al., *J. Neuropathol. Exp. Neurol.* 61:1013-1021 (2002); Bowman, et al., *Glia* 43:281-291 (2003)).

Rat primary astrocytes were obtained from prenatal rats and maintained for 14 days in culture before use. Embryos (E17-E19) were removed by caesarian section from a Sprague-Dawley rat and the hippocampi were surgically removed. The tissue was digested in trypsin/DNAse at 37° C., centrifuged (1000×5 min) and filtered to derive suspensions from each pup. Cells were grown in an incubator at 37° C. and 5% $CO_2$ in DMEM (Dulbecco's Modified Eagle's Medium; Bio-Whittaker/Cambrex BioScience, East Rutherford, N.J.), supplemented with Ham's F12 (Sigma-Aldrich, St. Louis, Mo.) and 5% fetal bovine serum (FBS) (Hyclone, Logan, Utah) for 7 days, followed by an additional 7 days in Neurobasal medium (Gibco, Grand Island, N.Y.) also supplemented with 5% FBS, 2 mM l-glutamine, 50 μg/ml streptomycin and 50 U/ml penicillin. In each experiment, the medium was changed to serum-free at 6-12 hours prior to addition of LPS, TNF-α, or gelsolin.

HAECs (primary human aortic endothelial cells) (ATCC, Rockville, Md. or Clonetics, San Diego, Calif.), will grow to confluence through passages 5-9 in endothelial cell growth medium supplemented with 2% fetal bovine serum, 10 μg/liter human recombinant epidermal growth factor, 1 mg/liter hydrocortisone, 50 μg/ml gentamicin, 50 ng/ml amphotericin-B, in a 37° C. humidified atmosphere of 95% air:5% $CO_2$.

HAECs and astrocytes cultures were incubated for 10 minutes in medium containing 10 μg/ml LPS alone, or LPS that had been pre-incubated with 0.16 mg/ml of human gelsolin. Cultures were fixed with ice-cold methanol and immunostained for F-actin with fluorescein isothiocyanate (FITC)-labeled phalloidin (Molecular Probes, Eugene, Oreg.). In astrocyte cultures, NF-κB translocation was manipulated by a 2 hour incubation in serum-free medium containing one of the following: 10 ng/ml TNF-α, 10 μg/ml LPS alone, or LPS that had been preincubated with 0.16 mg/ml human gelsolin. Location of transcription factor nuclear factor-kappaB (NF-κB) was observed using a monoclonal antibody to NF-κB (Molecular Probes), and cell nuclei were detected by counterstaining with 4', 6-diamidino-2-phenylindole dihydrochloride (DAPI) (Sigma).

Gelsolin binding to LPS also influenced in vitro cellular responses to LPS, protecting platelets, aortic endothelial cells (HAEC), as well as primary rat astrocytes, against LPS. At relatively high concentrations, LPS rapidly induced the disassembly of the actin cytoskeleton as seen in the disrupted and diffuse phalloidin staining in FIGS. 5B and 5E, compared to the abundant actin bundles seen in the controls (FIGS. 5A and 5D). However, when first incubated with an excess of plasma gelsolin, LPS had no discernable effect on the actin cytoskeletons of either HAEC or astrocytes.

More specifically, FIGS. 5A-5M show that LPS-induced-disruption of cellular responses was inhibited by pre-incubating the LPS with plasma gelsolin. Briefly, immunostaining for F-actin with phalloidin (FIGS. 5A-5F) was used to demonstrate that plasma gelsolin prevented LPS-induced actin cytoskeleton disassembly. Cultured human aortic endothelial cells (FIGS. 5A-5C) and primary rat astrocytes (FIGS. 5D-5F) were treated with 2 μM LPS (FIGS. 5B and 5E), or with 2 μM LPS and 1.8 μM gelsolin (FIGS. 5C and 5F). When the endothelial cells and astrocytes were exposed to LPS (10 μg/ml), disassembly of the actin cytoskeleton was readily induced as seen in the disrupted and diffuse phalloidin staining in FIGS. 5B and 5E, as compared to the abundant actin bundles in controls (FIGS. 5A and 5D). Control cells are shown in FIGS. 3A and 5D.

LPS is known to activate NF-κB, triggering induction of pro-inflammatory cytokine genes (see, Saura et al., *J. Neurochem*, 85:1455-67 (June 2003)). However, in the astrocytes the addition of 10 ng/ml TNF-α (FIGS. 5H and 5L), or 2 μM LPS (FIGS. 5I and 5M), caused NF-κB translocation to the nucleoplasm of the nucleus, as compared with control astrocytes, in which the NF-κB locates in the cytoplasm (FIGS. 5G and 5K). However, when first incubated (pre-incubated) with 1.8 μM of plasma gelsolin, LPS had no discernable effect on the actin cytoskeletons of either the endothelial cells or the astrocytes. The addition of gelsolin completely blocked the LPS-induced translocation of NF-κB (FIGS. 5G-4N), as shown by immunostaining for NF-κB with an antibody against NF-κB (FIGS. 5G-5J), and cell nuclei with DAPI (FIGS. 5L-5M). Preincubation with 1.8 μM gelsolin blocked LPS-induced translocation (FIGS. 5J and 4N).

Protective Effect of ORLFOVKGRR on LPS-Mediated Alteration of Platelet Function

To isolate human platelets, blood from healthy volunteers was collected in acid-citrate dextrose. Platelet-rich plasma obtained after centrifugation (15 minutes, 110×g) at room temperature, was supplemented with apyrase (0.5 U/ml) (Sigma-Aldrich) to degrade excess nucleotides. Platelets were sedimented by centrifugation (10 minutes, 1000×g), suspended in buffer A (139 mM NaCl, 2.8 mM KCl, 0.8 mM $MgCl_2$, 0.8 mM $KH_2PO_4$, 8.9 mM $NaHCO_3$, 10 mM HEPES, 5.6 mM glucose, 0.3% albumin, pH 7.35) and filtered on a 50 ml column of Sepharose 2B to obtain gel-filtered platelets (GFP).

Platelet aggregation was initiated by adding collagen (10 μg/ml) (Chrono-Log Corp., Havertown, Pa.). Platelet aggregation was monitored using a Chronolog Lumi-Aggregometer (Chrono-Log Corp.). Changes in light transmission were recorded for 10 minutes, using a PowerLab/200 instrument and MacLab Chart program Version 3.2. When required before activation, the platelet suspension was reacted with LPS, or LPS-preincubated with the SEQ ID No:1 peptide (QRLFQVKGRR).

A shown in FIG. 6, platelet aggregation was stimulated by collagen. When added alone, LPS strongly inhibited collagen-induced aggregation and secretion of platelets. Addition of gelsolin SEQ ID No:1 to LPS before its addition to platelets restored, in a peptide concentration-dependent manner, the normal collagen-induced platelets activation. However, gelsolin SEQ ID No:1 by itself had no effect on collagen-mediated platelet functions.

Example 5

Effect In Vivo of Plasma Gelsolin on Administered LPS

Since humans with sepsis have decreased plasma gelsolin concentrations, the effect of LPS administration on gelsolin levels was examined in mice. 6-7 week old, male, wild type C57BL/6 mice, each weighing 18-20 grams, purchased from Charles River Laboratories, Wilmington, Mass., are used for all animal studies. Mice are given free access to a standard feed and water, and all procedures and studies are approved by Harvard Medical Area Standing Committee on Animals according to standards as set forth in The Guide for the Care and Use of Laboratory Animals.

In a dose response assay, animals are injected i.p. (intraperitoneally) with LPS (*P. aeruginosa* Serotype 10, Sigma) at doses of 0, 10, 20, and 40 mg/kg. 3-4 animals are used in each group. 24 hours after administration of the LPS, the animals are anesthetized with Avertin i.p. (Fluka Chemie, Switzerland) at dose of 0.015-0.017 mg/g. Blood is then collected by retro-orbital bleeding into 0.1 volume of Aster-Jandl anticoagulant and centrifuged at 1000×g for 10 minutes. Plasma is aspirated and frozen in liquid nitrogen and stored in −80° C. until analyzed.

After sacrificing the anesthetized animals by cervical dislocation, peritoneal lavage is performed by injecting 3 ml of sterile PBS into the mouse peritoneal cavity. After gently messaging the abdomen, the fluid is aspirated by a syringe connected to a 22-gauge needle and centrifuged at 1000×g for 10 minutes to remove cellular contents. The supernatant fluid is collected and frozen in liquid nitrogen and stored at −80° C. until analyzed.

To study the effect on mortality, animals are injected i.p. with 25 mg/kg LPS (*E. coli* 055:B5, Sigma) and each mouse is randomly selected to receive one of the following three treatments: 1) GSN (containing: 8 mg of recombinant human plasma gelsolin (Biogen-IDEC, Inc) containing 1 mM Ca dissolved in 400 μl of 0.15 M NaCl (saline); or 2) BSA (containing: 8 mg of bovine albumin (Serologicals Proteins, Inc, Kankakee, Ill.) containing 1 mM Ca dissolved in 400 μl of saline, or 3) saline (containing only 400 μl saline). The GSN (gelsolin), BSA or saline solutions are administered subcutaneously at the dorsal surface of each animal immediately after LPS instillation, and then repeated at 24, 48, and 72 hours.

There are 9 mice in the saline group and 8 mice each in the GSN group and the BSA group. Animals are monitored frequently, and mortality is recorded and presented at an interval of days. Animal mortality study data are presented as Kaplan-Meier curves and log-rank test is used to analyze treatment impact on animal mortality. A p-value less than 0.05 is considered significant.

To measure gelsolin in vivo, a nucleation assay for plasma gelsolin is performed as follows: the collected mouse plasma is diluted 1:5 in Buffer B (0.1 M KCl, 0.2 mM $MgCl_2$, 1 mM EGTA (ethyleneglycol-bis(2-aminoethyl) N,N,N',N',-tetraacetic acid), 0.5 mM ATP, 0.5 mM β-mercaptoethanol, 10 mM Tris-HCl buffer, pH 7.4). From the diluted plasma sample, 5 μl is added to 280 μl Buffer B supplemented with 1.5 mm $CaCl_4$ and 0.4 μM phallacidin in 6×50 mm borosilicate culture tubes. The actin polymerization reaction is initiated by adding 15 μl 20 μM pyrene-actin in Buffer A (0.5 mM ATP, 0.5 mM β-mercaptoethanol, 0.2 mM $CaCl_2$ 0.2 mM Tris-HCl buffer, pH 7.4). Polymerization is monitored for 200 seconds in a spectrofluorimeter at excitation and emission wavelengths of 366 and 386 nm respectively. Gelsolin concentrations are estimated from a standard curve using recombinant human plasma gelsolin.

For all of fluorescence measurements in this or the foregoing Examples or in future assays, initial studies are done with a standard fluorimeter, for which a sample holder is adapted to preferably permit measurements from samples as small as 200 μL in disposable, pyrogen-free glass tubes. The pyrogen-free aspect is irrelevant for most studies since relatively larger amounts (ng/ml to μg/ml) of LPS will be added. But for other studies using specialized reagents, use of standard fluorimeter cuvettes is impractical since minimization of sample volume is needed to reduce the cost of the specialized reagents. The fluorescence intensity of PBP10 is high enough to read at 2 μM levels, and the fluorescence intensity will only go up when binding LPS.

Measurement of peritoneal lavage gelsolin is performed similarly, except 50 μl of peritoneal lavage and 30 μl of pyrene actin is used instead. Stock pyrene actin for these assays, prepared by the method of Kouyama and Mihashi (Kouyama et al., *Eur. J. Biochem.* 114:33-38 (1981), is stored at −80° C. in lots, thawed and diluted 10× with Buffer A, centrifuged at 250k×g for 30 minutes after standing overnight.

Plasma gelsolin is measured by the actin nucleation assay described above, and repeated (each assay was done in duplicate). All values are presented as mean±SD. A nonparametric test, Spearman Rank Correlation is used to analyze correlations in the dose response study. Mann-Whiney U-test is performed when comparing gelsolin levels. Plasma albumin levels are measured colorimetricly using a commercial kit (Stanbio Laboratory, Boerne, Tex.) according to the manufacture's instruction.

When mice receiving lethal doses of LPS intraperitoneally are treated with gelsolin (GSN), albumin (BSA) or saline, respectively, the exogenous plasma gelsolin rescues the endotoxemic mice. This is a dramatic response to gelsolin treatment, since mice receiving either the BSA or saline therapies, all die within 6 days of LPS treatment. See, PCT Appl. No. PCT/US04/037763. By comparison, after 1 week, the surviving mice (all in the GSN group) all appear to have complete recovery, and exhibit no signs of distress. The gelsolin amounts administered by this route restore plasma levels in LPS-treated animals to 200 μg/ml, which is slightly greater than the baseline concentrations (data not shown). Therefore, it can be concluded that animals treated in vivo with plasma gelsolin have markedly improved survival compared to those treated with saline or BSA controls.

Example 6

Function of Plasma Gelsolin in Vivo in Sepsis

Plasma Gelsolin as a Treatment for Sepsis

In light of the foregoing data in Example 5, suggesting that administration of exogenous plasma gelsolin can improve survival in endotoxemic animals, gelsolin-null and wild-type mice are exposed to similar endotoxemic challenge and determine if there are differences in survival and in markers of inflammation. Moreover, although it is not yet definitely known through which inflammation pathway, inflammation plasma gelsolin exerts its effect. Consequently, exogenous plasma gelsolin administration improves survival of wild-type septic animals, decreases secondary organ damage, and is associated with lower inflammatory mediators.

The general design of the experiment employs two different models of sepsis: 1) the LPS induced endotoxemia model, and 2) the cecal ligation puncture (CLP) mouse model. The main reason to develop the CLP model is that it more closely resembles clinical sepsis than LPS (Schultz et al., *Ann. Med.* 34:573-581 (2002)). In practice, gelsolin-null and genetically similar wild-type (C57BL/6) mice are subjected to injury (LPS or CLP). Two hours after injury, wild-type animals are divided randomly into 3 groups: 1) an experimental group given plasma gelsolin subcutaneously and 2 control groups: 2) a group given PBS; and 3) a control group given only BSA protein. Six animals from each group are then anesthetized and bled at various time points (4 hr, 16 hr, 28 hr, 40 hr), from which plasma will be generated.

The plasma samples are then analyzed for plasma gelsolin levels, as well as for inflammatory factors, TNF-α, IL-1β, and IL-6, since these mediators are known to increase during the development of sepsis (see, e.g., Riedemann et al., *J. Clin. Invest.* 112:460-467 (2003)). Furthermore, high mobility group B-1 (HMGB-1) protein is also measured, since this protein has been correlated with the delayed death of septic animals (Wang et al., *Science* 285:248-251 (1999)). To measure the secondary organ damage, plasma transaminases (ALT, AST), LDH, and creatinine are measured and compared. Additionally, there will be 10 animals in each arm of the study that are subjected to CLP in the "death as end point" study. Based on the data above, this number of animals is sufficient to most likely yield statistically significant differences in mortality between control and experimental animals.

Based upon the previous data, at least from Example 5 with LPS septic mice, gelsolin-null animals should have significantly higher mortality, higher inflammatory markers, and more severe secondary organ damage than the wild-type animals. Furthermore, plasma gelsolin treatment will significantly lower the mortality rate of wild-type animals subjected to CLP. Moreover, it is anticipated that gelsolin-treated animals will have less organ dysfunction reflected by lower levels of transaminases, LDH and creatinine. Results from CLP mice, therefore, lend more support to gelsolin as a promising therapeutic treatment in clinical sepsis.

The cytokine profile differs somewhat between LPS and CLP models of sepsis, especially in TNF-α production (Villa et al., *Clin. Diagn. Lab. Immunol.* 2:549-553 (1995)). In the LPS model, TNF-α is intensely elevated within 2 hours of challenge (see Rothenbach et al., 2004, supra.); whereas in the CLP model, TNF-α is only mildly elevated. Since the present animals are treated 2 hours after injury, it is likely that TNF-α pathway has already been initiated, and gelsolin treatment is unlikely to affect TNF-α levels. On the other hand IL-1β and IL-6 are elevated in both the LPS and CLP models, and tend to stay elevated for many hours, meaning that gelsolin treatment may affect these 2 cytokines in reducing inflammation. HMGB-1 appears later in the course of sepsis, and is associated with lethality (Wang et al., 1999, supra). As a result, gelsolin treatment may decrease blood HMGB-1 levels, reflecting the rescue effect of the gelsolin treatment.

Given that a preliminary study on trauma patients shows that there is a significant difference in the plasma gelsolin levels between surviving and non-surviving critically ill patients, the study is extended to include plasma gelsolin levels in patients with sepsis, burns and ARDS. In general, discarded anti-coagulated blood is collected that has been drawn from the patients. Plasma is generated from each sample and flash-frozen in liquid nitrogen and stored in −80° C. until measurements of plasma gelsolin and albumin levels are performed. For each patient, the follow data are recorded: APACHE II scores, ventilated time, ICU days, hospital days, age, gender, race, development of ARDS and sepsis, ICU mortality and hospital mortality. The primary end points of the study include ICU mortality and hospital mortality. Secondary end points include 30-day ICU free days, 30-day ventilator-free hours, development of ARDS, and sepsis.

By assuming alpha=0.05 (thereby establishing a p value of 0.05), the estimated incidence of ARDS and sepsis will equal about 15%, which determines the sample size needed to generate an 80% power of a two-sided Fisher's exact test being able to detect an OR of 10.28 (which is the estimated relative risk of ARDS or sepsis of patients with very low gelsolin, compared to low to normal gelsolin levels) between very low plasma gelsolin and development of ARDS or sepsis is 67 patients. It is expected that there will be a significant difference in plasma gelsolin levels between survivors and non-survivors in the MICU, as supported by above studies. Moreover, it is further expect that those with very low plasma gelsolin levels will have significantly shorter ICU-free days, ventilator-free hours and will be at higher risk of developing ARDS and/or sepsis. Albumin level serves as the control protein to show that depression of plasma gelsolin is not simply representative of a non-specific low protein state, which conclusion is also supported by the data above.

Example 7

Gelsolin Blocks LTA-mediated Leukocyte Activation

To investigate whether gelsolin can prevent gram-positive bacterial inflammation, the effect of LTA-mediated activation of human neutrophils was examined. Neutrophils were selected because their adhesion to human aorta endothelial cells (HAEC) is a hallmark of inflammation. The data showed that gelsolin does, in fact, inhibit neutrophil adhesion to LTA-stimulate human endothelial cells.

As shown in FIG. 7, LTA from gram-positive bacteria interacts with gelsolin in much the same way as LPS from gram-negative bacteria were shown to interact with gelsolin above. In fact, LTA inhibits gelsolin to sever actin nearly as well as LPS does.

Materials and Methods:

The tested gelsolin concentration was 50 nM; LTA ranged from 0-50 µM; Pyrene-F-actin was 0.3 µM. Recording changes in fluorescently-labeled (rhodamine B-labeled)

gelsolin peptide PBP10 (10 μM), indicates a specific interaction between gelsolin and LTA. LTA bound to gelsolin with approximately the same avidity as PIP2, thereby inhibiting the actin-severing capability of gelsolin.

Neutrophils were isolated from human blood using the endotoxin-free Lympholyte-poly kit (Cedarlane, Ontario, Canada). The isolated neutrophil cells were resuspended in RPMI media. The addition of LTA (10 μg/ml) to HAECs stimulated binding of calcein AM-labeled neutrophils to the endothelial surface (Kawamura et al., *Biochem. Biophys. Res Commun.* 217:1208-1215 (1995)). However, when physiological concentrations of gelsolin (2 μM) were added along with LTA, neutrophil adhesion was reduced to near baseline values. To quantify the adhesion, the neutrophils were labeled with calcein-AM (5 μM for 30 minutes at 37° C.).

Consequently, while gelsolin binding to LTA inhibits gelsolin's severing function, gelsolin also inhibits the ability to LTA to promote neutrophil adhesion to the endothelium. Thus, a method is provided for using gelsolin to inhibit or block inflammation, which involved neutrophil adhesion to the endothelium, and further offers a method of interaction with LTA to treat gram-positive sepsis. Moreover, a similar effect was shown in FIG. 9, wherein bioactive eukaryotic lysophospholipid mediators of cell function, such as sphingosine 1-phosphate (S1P) and sphingosyl phosphocoline (SPC), also inhibit gelsolin (50 nM), at least as strongly as lysophosphatidic acid (LPA) when added at concentrations below 1 μM. S1P is also a potent bioactive signal that increases following the onset of bacterial sepsis and other inflammatory disorders. Although details of the mechanism for this response are not yet clear, part of gelsolin's effect on endotoxemia may be through binding of S1P and SPC. As a result, not only does the present invention provide a method for treating LPS-mediated gram-negative sepsis, the demonstrated interaction of gelsolin with LTA further provides a method for treating gram positive sepsis.

The disclosures of each patent, patent application and publication cited or described in this document are hereby incorporated herein by reference, in their entirety.

While the foregoing specification has been described with regard to certain preferred embodiments, and many details have been set forth for the purpose of illustration, it will be apparent to those skilled in the art without departing from the spirit and scope of the invention, that the invention may be subject to various modifications and additional embodiments, and that certain of the details described herein can be varied considerably without departing from the basic principles of the invention. Such modifications and additional embodiments are also intended to fall within the scope of the appended claims.

What is claimed is:

1. A method of reducing risk of septic shock in a patient who is infected with bacteria, and who is at risk of septic shock, the method comprising:
   (a) measuring a blood gelsolin concentration of a patient who is infected with bacteria;
   (b) determining that the patient is at risk of septic shock if the blood gelsolin concentration of the patient is less than 30% of matched, pre-infection, pre-trauma control subjects, but not at risk of septic shock if the circulating gelsolin concentration of the patient is greater than 30% of matched, pre-infection, pre-trauma control subjects; and
   (c) parenterally administering gelsolin to the patient if the patient has been determined to be at risk of septic shock.

2. A method of reducing risk of septic shock in a patient who is infected with gram-positive bacteria, and who is at risk of by gram-positive bacterium-induced sepsis, the method comprising:
   (a) measuring a blood gelsolin concentration of a patient who is infected with gram-positive bacteria;
   (b) determining that the patient is at risk of gram-positive bacterium-induced sepsis if the blood gelsolin concentration of the patient is less than 30% of matched, pre-infection, pre-trauma control subjects, but not at risk of gram-positive bacterium-induced sepsis if the circulating gelsolin concentration of the patient is greater than 30% of matched, pre-infection, pre-trauma control subjects; and
   (c) parenterally administering gelsolin to the patient if the patient has been determined to be at risk of gram-positive bacterium-induced sepsis.

3. The method of claim 1, wherein the bacterial infection releases endotoxin lipoteichoic acid (LTA).

4. The method of claim 3, wherein the lipoteichoic acid (LTA) is released from a gram-positive bacterium.

5. The method of claim 4, wherein the gram-positive bacterium is *Streptococcus pneumoniae* or *Staphylococcus aureus*.

6. The method of claim 2, wherein the gram-positive bacterium is *Streptococcus pneumoniae* or *Staphylococcus aureus*.

7. The method of claim 1, wherein the bacterial infection releases endotoxin lipopolysaccharide (LPS).

8. The method of claim 7, wherein the lipopolysaccharide (LPS) is released from a gram-negative bacterium.

9. The method of claim 8, wherein the gram-negative bacterium is *Escherichia coli, Salmonella enteriditis* or *Klebsiella pneumoniae*.

SEQUENCE LISTING

```
<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: peptide fragment of gelsolin

<400> SEQUENCE: 1

Gln Arg Leu Phe Gln Val Lys Gly Arg Arg
1               5                   10
```

10. The method of claim 1, wherein the gelsolin is administered intravenously, intramuscularly, intraperitoneally, or subcutaneously.

11. The method of claim 2, wherein the gelsolin is administered intravenously, intramuscularly, intraperitoneally, or subcutaneously.

12. The method of claim 1 further comprising administering to the patient an expression vector containing a nucleic acid which encodes gelsolin.

13. The method of claim 2 further comprising administering to the patient an expression vector containing a nucleic acid which encodes gelsolin.

* * * * *